US011193862B2

(12) United States Patent
Ivosevic et al.

(10) Patent No.: US 11,193,862 B2
(45) Date of Patent: Dec. 7, 2021

(54) BIOLOGICAL FLUID COLLECTION DEVICE AND COLLECTION MODULE

(71) Applicant: Becton, Dickinson and Company, Franklin Lakes, NJ (US)

(72) Inventors: Milan Ivosevic, Kinnelon, NJ (US); Adam Edelhauser, Kinnelon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 161 days.

(21) Appl. No.: 16/285,659

(22) Filed: Feb. 26, 2019

(65) Prior Publication Data
US 2019/0265134 A1 Aug. 29, 2019

Related U.S. Application Data

(60) Provisional application No. 62/634,960, filed on Feb. 26, 2018.

(51) Int. Cl.
*G01N 1/38* (2006.01)
*A61B 5/15* (2006.01)
(Continued)

(52) U.S. Cl.
CPC ............ *G01N 1/38* (2013.01); *A61B 5/15003* (2013.01); *A61B 5/154* (2013.01); *A61B 5/15074* (2013.01); *A61B 5/150213* (2013.01); *A61B 5/150221* (2013.01); *A61B 5/150251* (2013.01); *A61B 5/150351* (2013.01);
(Continued)

(58) Field of Classification Search
CPC ............ G01N 1/38; G01N 33/49; G01N 1/14; G01N 2001/386; B01L 3/502; B01L 2300/048; B01L 2400/0481; B01L 2400/049; B01L 2300/0838; B01L 2300/0832; B01L 2200/0605; B01L 2300/0609; B01L 3/0296; B01L 2300/087; A61B 5/15074; A61B 5/150351; A61B 5/15003; A61B 5/150732; A61B 5/154;
(Continued)

(56) References Cited

U.S. PATENT DOCUMENTS

2005/0054949 A1* 3/2005 McKinnon ....... A61B 5/150213
600/576
2009/0259145 A1* 10/2009 Bartfeld ............. A61B 10/0096
600/576
(Continued)

FOREIGN PATENT DOCUMENTS

JP 2016518921 A 6/2016
JP 2017531782 A 10/2017

*Primary Examiner* — Ryan D Walsh
(74) *Attorney, Agent, or Firm* — The Webb Law Firm

(57) ABSTRACT

A biological fluid collection device that receives a sample and provides flow-through blood stabilization technology and a precise sample dispensing function for point-of-care and near patient testing applications is disclosed. A biological fluid collection device of the present disclosure is able to effectuate distributed mixing of a sample stabilizer within a blood sample and dispense the stabilized sample in a controlled manner. In this manner, a biological fluid collection device of the present disclosure enables blood micro-sample management, e.g., passive mixing with a sample stabilizer and controlled dispensing, for point-of-care and near patient testing applications.

19 Claims, 17 Drawing Sheets

(51) Int. Cl.
*G01N 1/14* (2006.01)
*B01L 3/00* (2006.01)
*G01N 33/49* (2006.01)
*A61B 5/154* (2006.01)
*B01L 3/02* (2006.01)

(52) U.S. Cl.
CPC .. *A61B 5/150732* (2013.01); *A61B 5/150755* (2013.01); *B01L 3/502* (2013.01); *G01N 1/14* (2013.01); *G01N 33/49* (2013.01); *B01L 3/0296* (2013.01); *B01L 2200/0605* (2013.01); *B01L 2300/048* (2013.01); *B01L 2300/0609* (2013.01); *B01L 2300/087* (2013.01); *B01L 2300/0832* (2013.01); *B01L 2300/0838* (2013.01); *B01L 2400/049* (2013.01); *B01L 2400/0481* (2013.01); *G01N 2001/386* (2013.01)

(58) Field of Classification Search
CPC ........ A61B 5/150755; A61B 5/150213; A61B 5/150251; A61B 5/150221
See application file for complete search history.

(56) References Cited

U.S. PATENT DOCUMENTS

| | | |
|---|---|---|
| 2014/0309551 A1 | 10/2014 | Burkholz et al. |
| 2016/0262679 A1* | 9/2016 | Ivosevic ............ A61B 5/15003 |
| 2016/0367177 A1* | 12/2016 | Edelhauser ...... A61B 5/150221 |
| 2017/0035337 A1* | 2/2017 | Wilkinson ....... A61B 5/150969 |
| 2017/0059550 A1 | 3/2017 | Rao et al. |
| 2017/0216835 A1 | 8/2017 | Ivosevic et al. |
| 2018/0021026 A1* | 1/2018 | Nelson ................... B01L 3/505 422/507 |

* cited by examiner

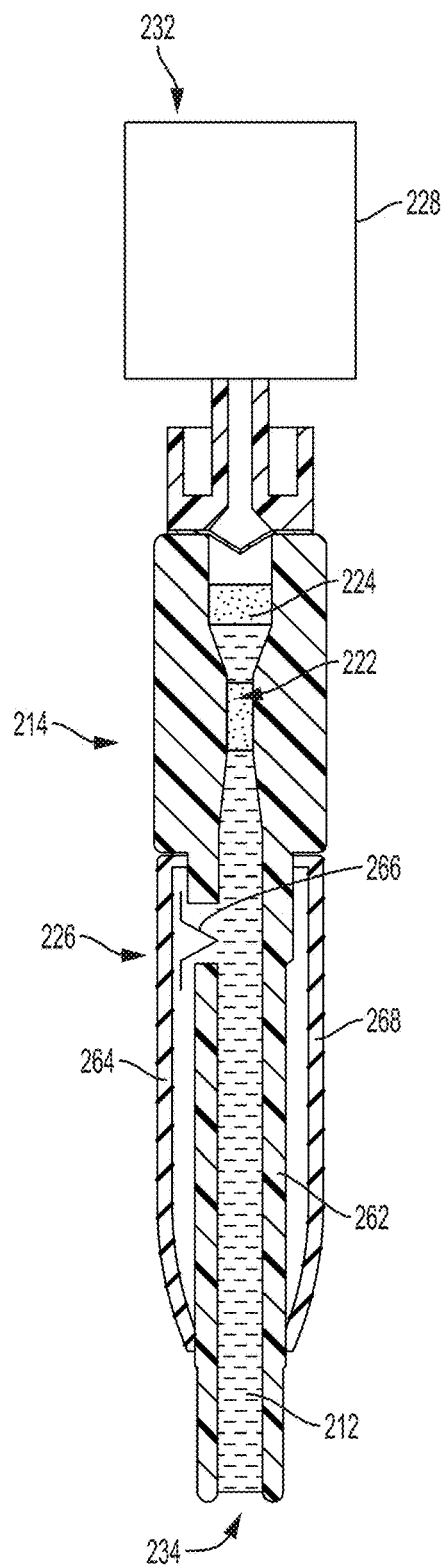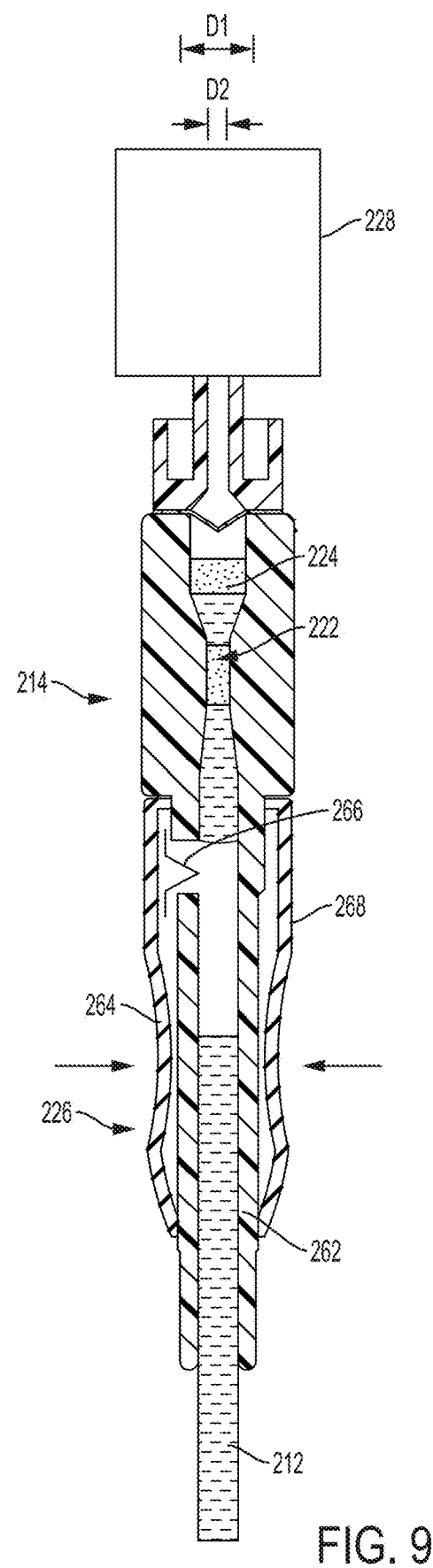
FIG. 8
FIG. 9

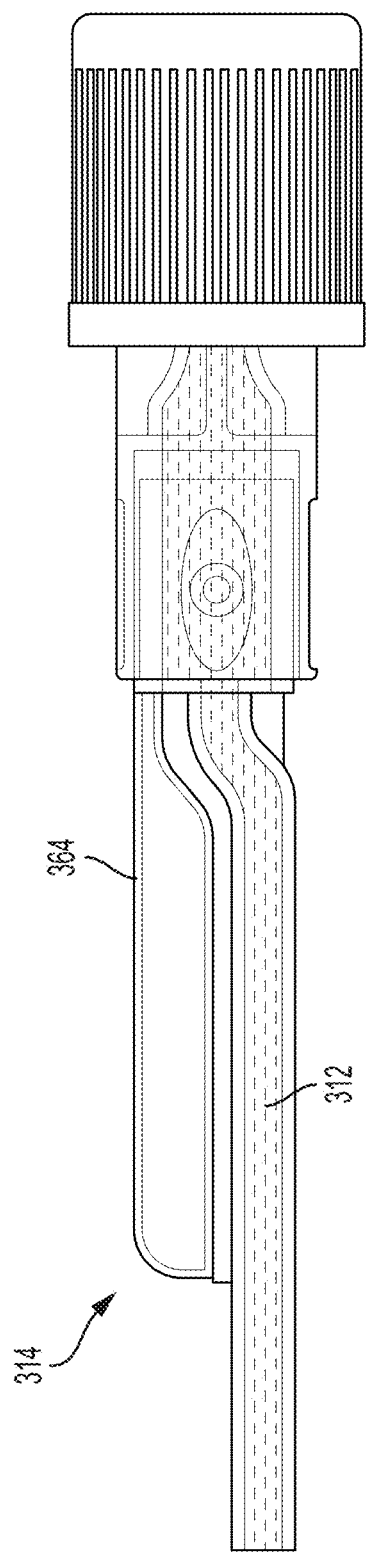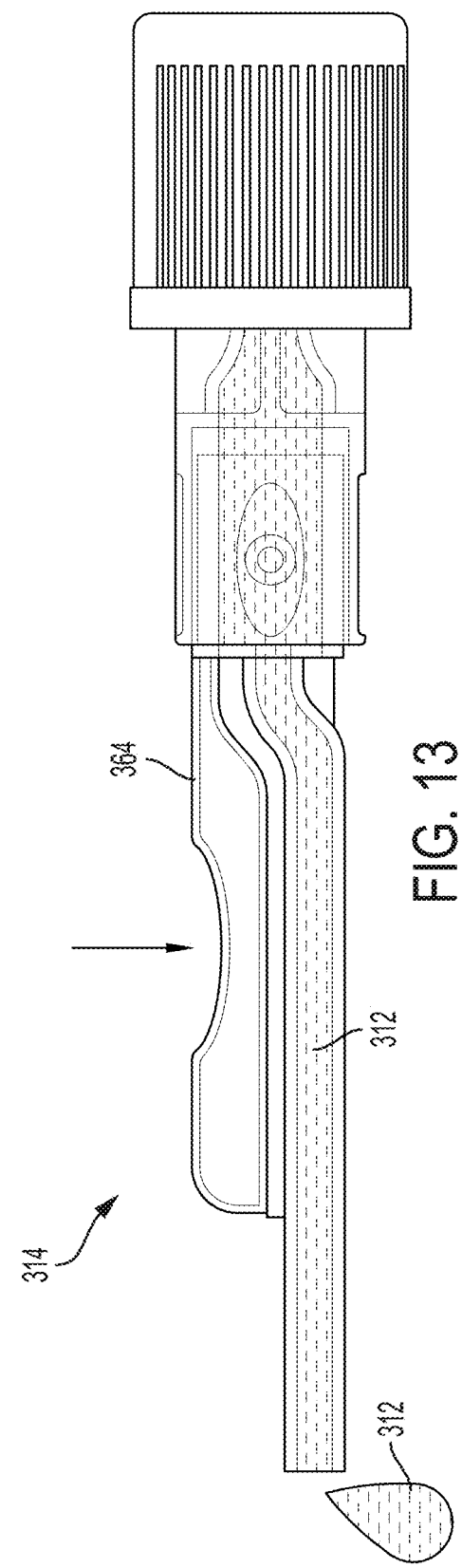
FIG. 12
FIG. 13

BIOLOGICAL FLUID COLLECTION DEVICE AND COLLECTION MODULE

CROSS-REFERENCE TO RELATED APPLICATION

The present application claims priority to U.S. Provisional Application Ser. No. 62/634,960, filed Feb. 26, 2018, entitled "Biological Fluid Collection Device and Collection Module", the entire disclosure of which is hereby incorporated by reference.

BACKGROUND OF THE INVENTION

1. Field of the Disclosure

The present disclosure relates generally to a biological fluid collection device. More particularly, the present disclosure relates to a collection module for collecting a small sample of blood and dispensing a portion of the sample into a device for analyzing the sample such as a point-of-care or a near-patient-testing device.

2. Description of the Related Art

A need exists for a device which enables collection of a micro-sample, such as less than 500 microliters of collected sample for analysis, for patient point-of-care applications. Current devices require conventional sample collection and the subsequent use of a 1 ml syringe or pipette to transfer a small blood sample to a point-of-care cartridge or instrument receiving port. Such an open system approach results in an increased blood exposure risk for personnel performing the testing, as well as the collection of excess specimen required for a specified test procedure.

It is therefore desirable to have a blood sample collection and dispensing tool for point-of-care applications which incorporates conventional automatic blood draw and includes a novel controlled sample dispensing capability while minimizing exposure risk.

SUMMARY OF THE INVENTION

The present disclosure provides a biological fluid collection device that receives a sample and provides flow-through blood stabilization technology and a precise sample dispensing function for point-of-care and near patient testing applications. A biological fluid collection device of the present disclosure is able to effectuate distributed mixing of a sample stabilizer within a blood sample and dispense the stabilized sample in a controlled manner. In this manner, a biological fluid collection device of the present disclosure enables blood micro-sample management, e.g., passive mixing with a sample stabilizer and controlled dispensing, for point-of-care and near patient testing applications.

In accordance with an embodiment of the present invention, a collection module adapted to receive a sample includes a housing having an inlet port and an outlet port, the inlet port and the outlet port in fluid communication; a mixing chamber disposed between the inlet port and the outlet port; a sample stabilizer disposed between the inlet port and the mixing chamber; and a collection chamber disposed between the mixing chamber and the outlet port, the collection chamber including a first deformable portion and a second deformable portion.

In one configuration, the first deformable portion and the second deformable portion are transitionable between an initial position in which the sample is contained within the collection chamber and a deformed position in which a portion of the sample is expelled from the collection chamber. In another configuration, the first deformable portion and the second deformable portion are simultaneously squeezed to transition from the initial position to the deformed position. In yet another configuration, the collection chamber further comprises a rigid wall portion between the first deformable portion and the second deformable portion. In one configuration, the mixing chamber receives the sample and the sample stabilizer therein. In another configuration, the mixing chamber effectuates distributed mixing of the sample stabilizer within the sample. In yet another configuration, the mixing chamber further comprises a first curved wall having a first inlet end and a first exit end; and a second curved wall having a second inlet end and a second exit end, wherein the first inlet end is spaced a first distance from the second inlet end, and wherein the first exit end is spaced a second distance from the second exit end, the second distance less than the first distance. In one configuration, the collection module further comprises a material including pores disposed between the inlet port and the mixing chamber; and a dry anticoagulant powder within the pores of the material. In another configuration, the sample dissolves and mixes with the dry anticoagulant powder while passing through the material. In yet another configuration, the material is an open cell foam. In one configuration, the sample stabilizer is the dry anticoagulant powder. In another configuration, the collection module further comprises a closure covering the inlet port. In yet another configuration, the collection module further comprises a cap covering the outlet port and having a venting plug which allows air to pass therethrough and prevents the sample from passing therethrough. In one configuration, the sample is a blood sample. In another configuration, a biological fluid collection device comprises a collection module adapted to receive a sample that includes a housing having an inlet port and an outlet port, the inlet port and the outlet port in fluid communication; a mixing chamber disposed between the inlet port and the outlet port; a sample stabilizer disposed between the inlet port and the mixing chamber; and a collection chamber disposed between the mixing chamber and the outlet port, the collection chamber including a first deformable portion and a second deformable portion; and an outer housing removably connectable to the collection module, wherein, with the collection module connected to the outer housing, the collection module is disposed within the outer housing.

In accordance with another embodiment of the present invention, a collection module adapted to receive a sample includes a housing having an inlet port and an outlet port, the inlet port and the outlet port in fluid communication; a mixing chamber disposed between the inlet port and the outlet port; a sample stabilizer disposed between the inlet port and the mixing chamber; and a collection chamber disposed between the mixing chamber and the outlet port, the collection chamber comprising: a rigid wall chamber that receives the sample; a deformable portion including air, the deformable portion external to the rigid wall chamber; and a one-way valve between the rigid wall chamber and the deformable portion, wherein the deformable portion is transitionable between an initial position in which the sample is contained within the rigid wall chamber and a deformed position in which a portion of the sample is expelled from the rigid wall chamber, and wherein the one-way valve prevents the sample from moving from the rigid wall chamber to the deformable portion and allows air to move from the deformable portion to the rigid wall chamber to expel the sample from the rigid wall chamber.

In one configuration, the deformable portion comprises a bladder. In another configuration, the mixing chamber receives the sample and the sample stabilizer therein. In yet another configuration, the mixing chamber effectuates distributed mixing of the sample stabilizer within the sample. In one configuration, the mixing chamber further comprises a first curved wall having a first inlet end and a first exit end; and a second curved wall having a second inlet end and a second exit end, wherein the first inlet end is spaced a first distance from the second inlet end, and wherein the first exit end is spaced a second distance from the second exit end, the second distance less than the first distance. In another configuration, the collection module further comprises a material including pores disposed between the inlet port and the mixing chamber; and a dry anticoagulant powder within the pores of the material. In yet another configuration, the sample dissolves and mixes with the dry anticoagulant powder while passing through the material. In one configuration, the material is an open cell foam. In another configuration, the sample stabilizer is the dry anticoagulant powder. In yet another configuration, the collection module further comprises a closure covering the inlet port. In one configuration, the collection module further comprises a cap covering the outlet port and having a venting plug which allows air to pass therethrough and prevents the sample from passing therethrough. In another configuration, the sample is a blood sample. In yet another configuration, a biological fluid collection device comprises a collection module adapted to receive a sample that includes a housing having an inlet port and an outlet port, the inlet port and the outlet port in fluid communication; a mixing chamber disposed between the inlet port and the outlet port; a sample stabilizer disposed between the inlet port and the mixing chamber; and a collection chamber disposed between the mixing chamber and the outlet port, the collection chamber comprising: a rigid wall chamber that receives the sample; a deformable portion including air, the deformable portion external to the rigid wall chamber; and a one-way valve between the rigid wall chamber and the deformable portion, wherein the deformable portion is transitionable between an initial position in which the sample is contained within the rigid wall chamber and a deformed position in which a portion of the sample is expelled from the rigid wall chamber, and wherein the one-way valve prevents the sample from moving from the rigid wall chamber to the deformable portion and allows air to move from the deformable portion to the rigid wall chamber to expel the sample from the rigid wall chamber; and an outer housing removably connectable to the collection module, wherein, with the collection module connected to the outer housing, the collection module is disposed within the outer housing.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 8 is a cross-sectional side elevation view of a collection module with a deformable portion in an initial position in accordance with another embodiment of the present invention.

FIG. 9 is a cross-sectional side elevation view of a collection module with a deformable portion in a deformed position in accordance with another embodiment of the present invention.

FIG. 12 is a partial cross-sectional view of a collection module with a deformable portion in an initial position in accordance with another embodiment of the present invention.

FIG. 13 is a partial cross-sectional view of a collection module with a deformable portion in a deformed position in accordance with another embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1A:
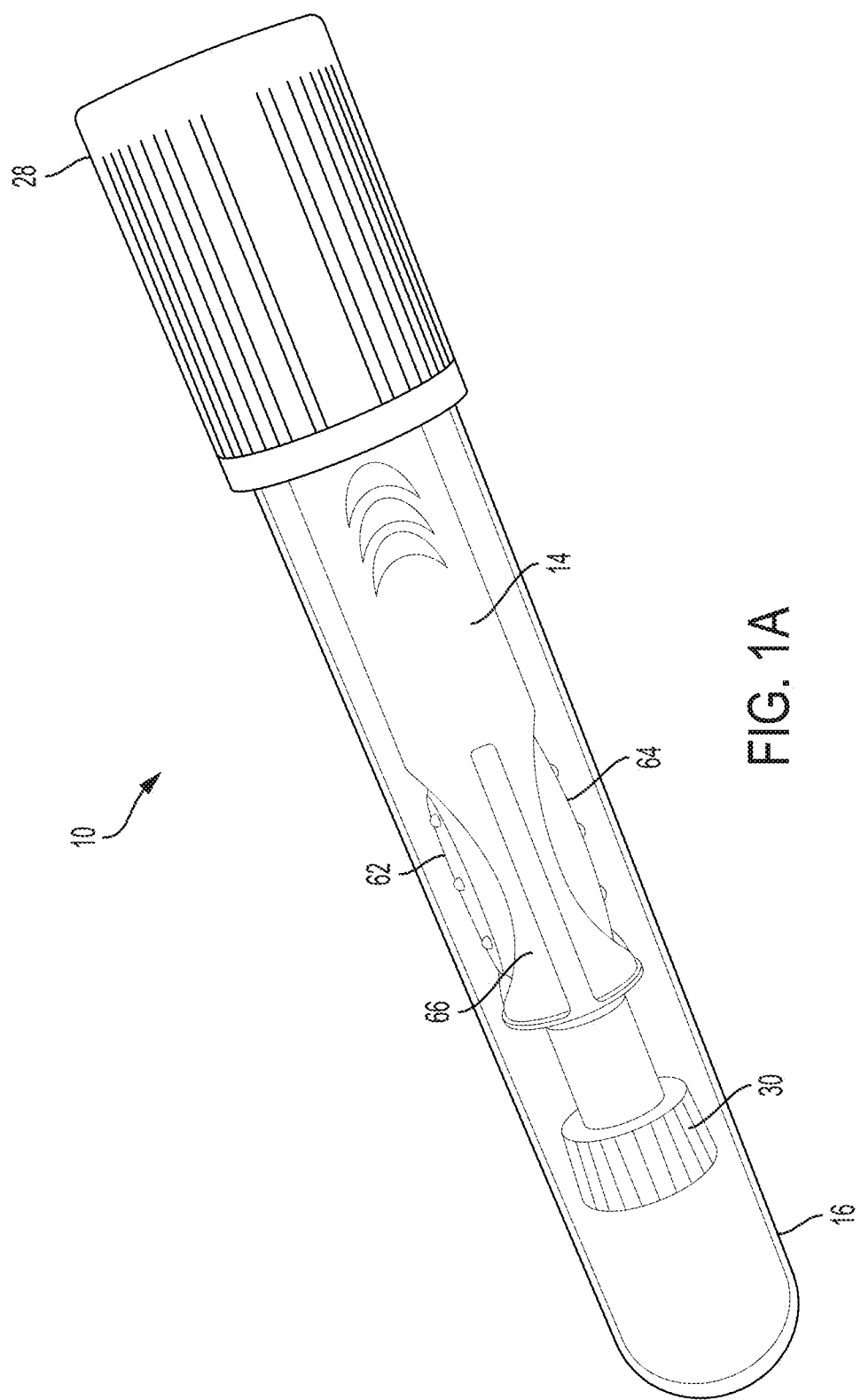
FIG. 1A is a perspective view of a biological fluid collection device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

The present disclosure provides a biological fluid collection device that receives a sample and provides flow-through blood stabilization technology and a precise sample dispensing function for point-of-care and near patient testing applications. A biological fluid collection device of the present disclosure is able to effectuate distributed mixing of a sample stabilizer within a blood sample and dispense the stabilized sample in a controlled manner. In this manner, a biological fluid collection device of the present disclosure enables blood micro-sample management, e.g., passive mixing with a sample stabilizer and controlled dispensing, for point-of-care and near patient testing applications.

Advantageously, a biological fluid collection device of the present disclosure provides a consistent blood sample management tool for point-of-care and near patient testing applications, automatic blood draw, passive mixing technology, and controlled small sample dispensing capability to point-of-care cartridge and standard luer interfaces with near patient testing receiving ports.

Figure 1B:
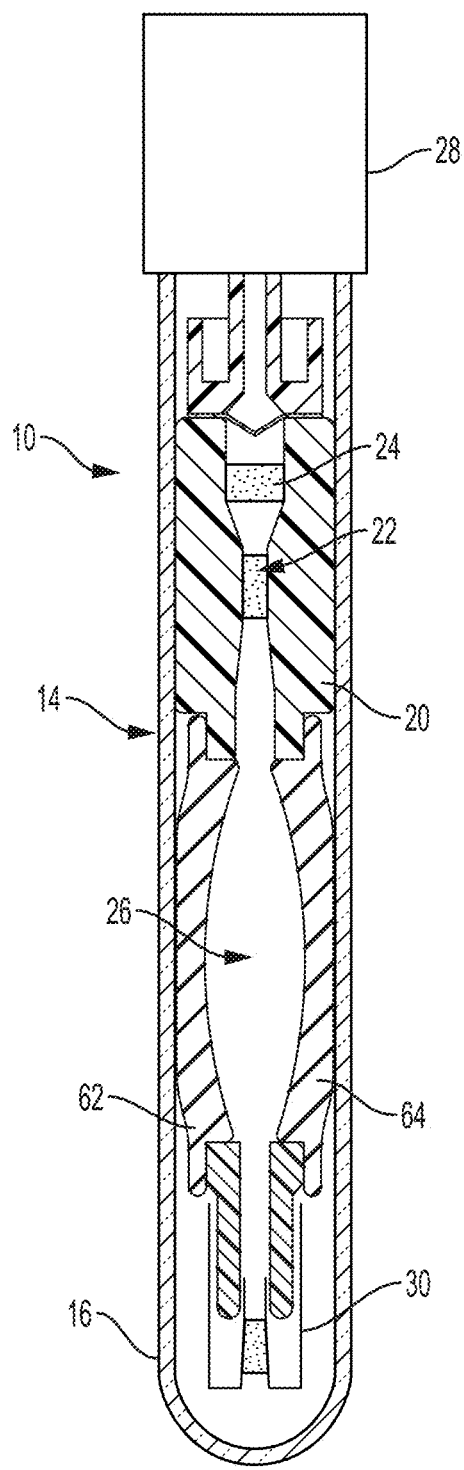
FIG. 1B is a cross-sectional side elevation view of a biological fluid collection device in accordance with an embodiment of the present invention.
Figure 2:
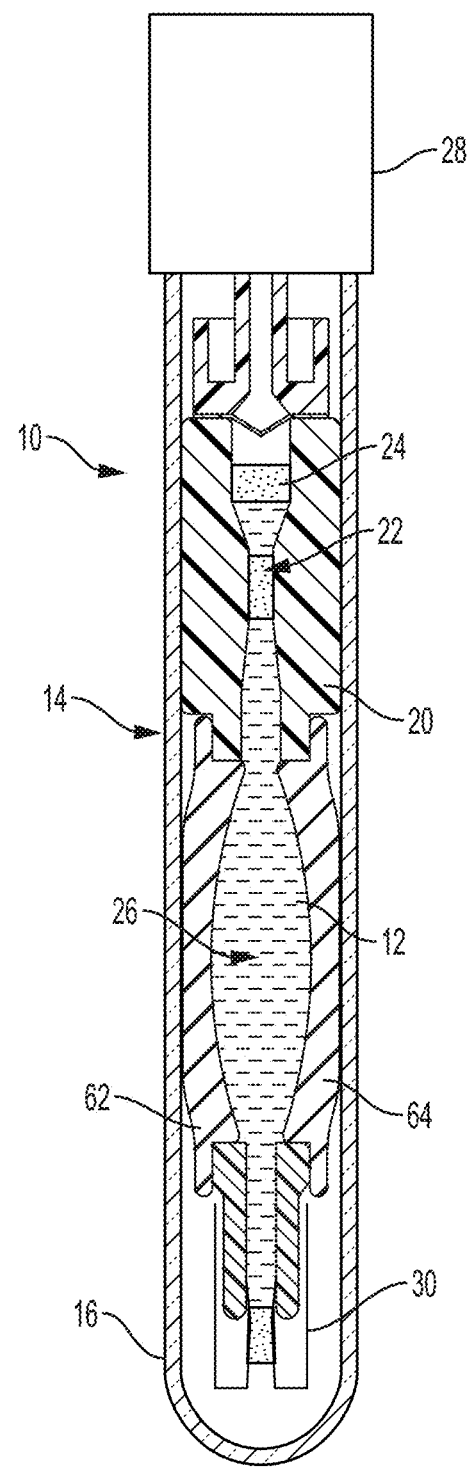
FIG. 2 is a cross-sectional side elevation view of a biological fluid collection device with a biological sample in accordance with an embodiment of the present invention.
Figure 3:
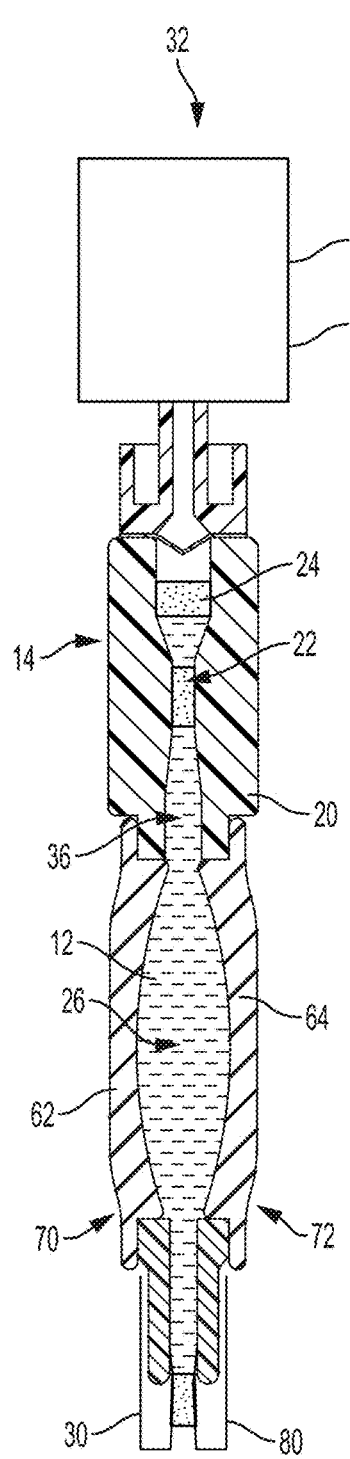
FIG. 3 is a cross-sectional side elevation view of a collection module with a cap in accordance with an embodiment of the present invention.
Figure 4:
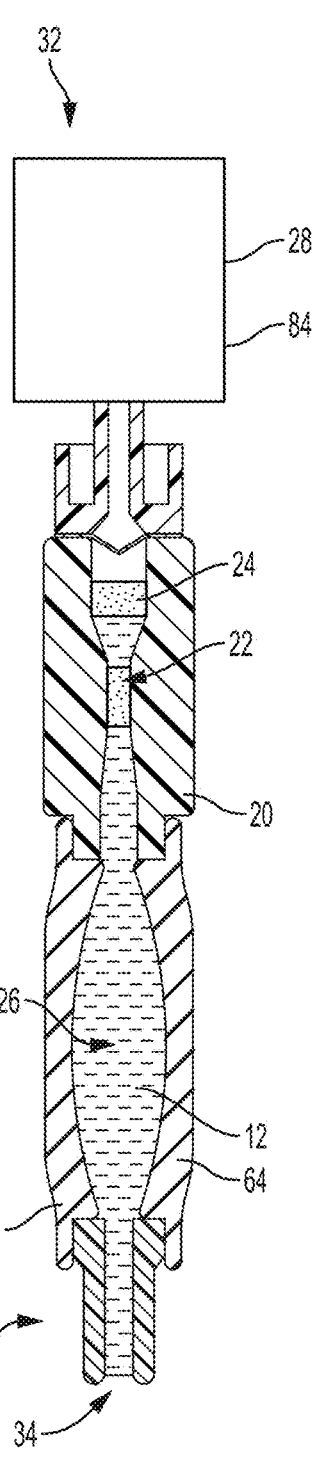
FIG. 4 is a cross-sectional side elevation view of a collection module with a deformable portion in an initial position in accordance with an embodiment of the present invention.

FIGS. 1A-5 illustrate an exemplary embodiment of a biological fluid collection device of the present disclosure. Referring to FIGS. 1A-2, a biological fluid collection device 10 of the present disclosure is adapted to receive a biological fluid sample, such as a blood sample 12, and includes a collection module 14 and an outer housing 16 that is removably connectable to the collection module 14. In one embodiment, with the collection module 14 connected to the outer housing 16, the collection module 14 is disposed within the outer housing 16 as shown in FIGS. 1A-2.

Referring to FIGS. 1A-5, in one embodiment, the collection module 14 of the present disclosure is adapted to receive a biological fluid sample, such as a blood sample 12, and includes a housing 20, a mixing chamber 22, a sample stabilizer 24, a collection chamber 26, a closure 28, and a cap 30.

In one embodiment, the housing 20 of the collection module 14 includes an inlet port 32 and an outlet port 34. In one embodiment, the inlet port 32 and the outlet port 34 are in fluid communication via a passageway 36 extending therebetween.

The mixing chamber 22 and the collection chamber 26 are provided in fluid communication via the passageway 36. The mixing chamber 22 and the collection chamber 26 are positioned such that a biological fluid sample, such as a blood sample 12, introduced into the inlet port 32 of the collection module 14 will first pass through a sample stabilizer 24, then the blood sample 12 and the sample stabilizer 24 pass through the mixing chamber 22, and subsequently the sample 12 with the sample stabilizer 24 properly mixed therein flow into the collection chamber 26, prior to reaching the outlet port 34 of the collection module 14. In this way, the blood sample 12 may be mixed with a sample stabilizer 24, such as an anticoagulant or other additive, provided within the collection module 14, before passing through the mixing chamber 22 for proper mixing of the sample stabilizer 24 within the blood sample 12, and then the stabilized sample is received and stored within the collection chamber 26.

In one embodiment, a sample stabilizer 24 is disposed between the inlet port 32 and the mixing chamber 22. The collection module 14 of the present disclosure provides passive and fast mixing of a blood sample 12 with the sample stabilizer 24. For example, the collection module 14 includes a mixing chamber 22 that allows for passive mixing of the blood sample 12 with an anticoagulant or another additive, such as a blood stabilizer, as the blood sample 12 flows through the mixing chamber 22.

The sample stabilizer can be an anticoagulant, or a substance designed to preserve a specific element within the blood such as, for example, RNA, protein analyte, or other element. In one embodiment, the sample stabilizer 24 is disposed between the inlet port 32 and the mixing chamber 22. In other embodiments, the sample stabilizer 24 may be disposed in other areas within the housing 20 of the collection module 14.

Figure 14:
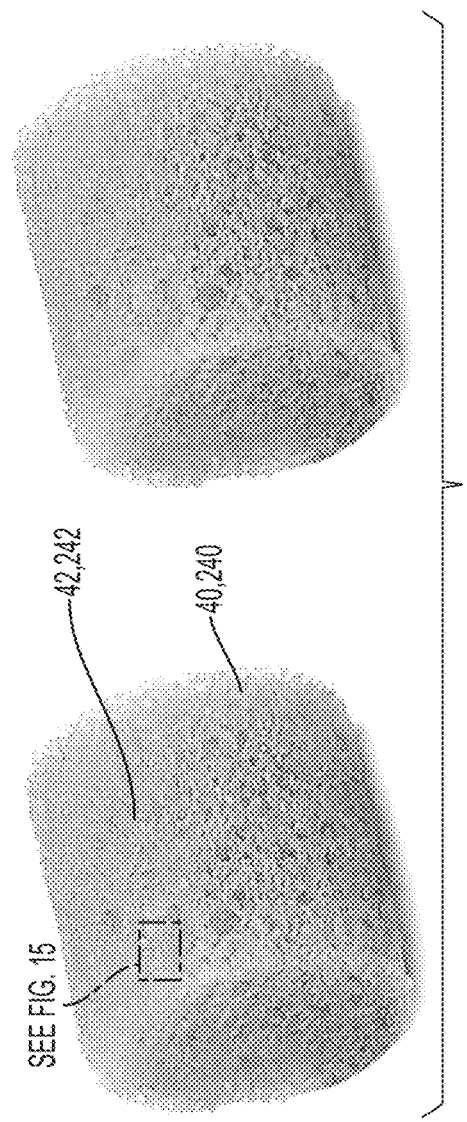
FIG. 14 is a perspective view of an open cell foam material in accordance with an embodiment of the present invention.
Figure 15:
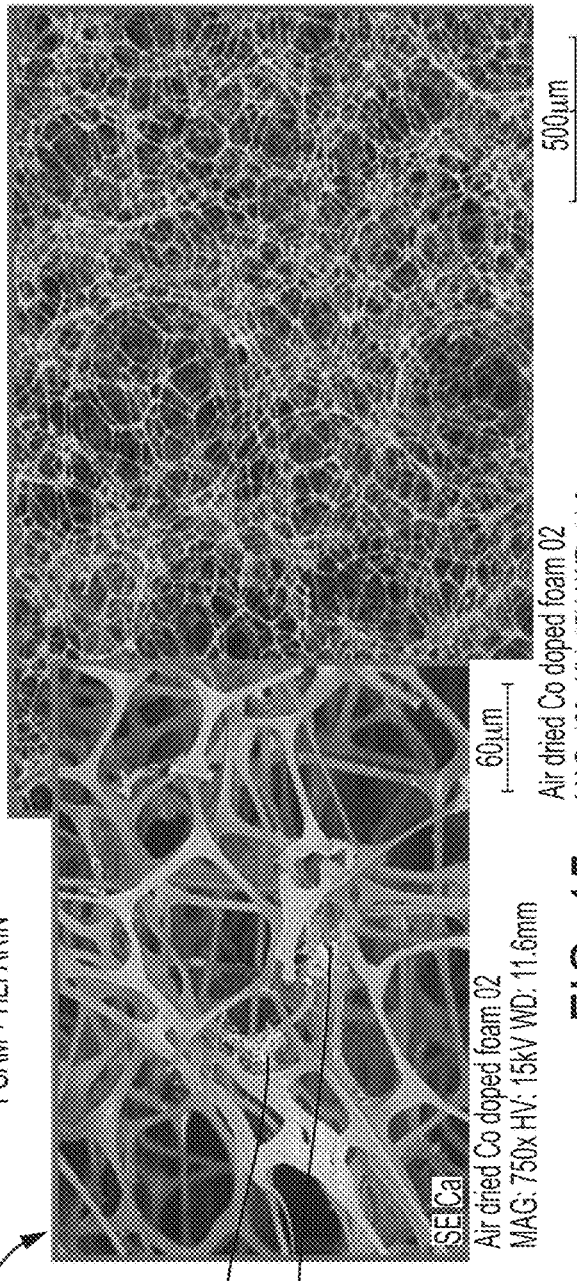
FIG. 15 is a microscopic view of the microstructure of an open cell foam material having a dry anticoagulant powder distributed throughout its microstructure in accordance with an embodiment of the present invention.

Referring to FIGS. 14 and 15, in one embodiment, the collection module 14 includes a material 40 including pores 42 that is disposed between the inlet port 32 and the mixing chamber 22 and a dry anticoagulant powder 44 that is within the pores 42 of the material 40. In this manner, the collection module 14 may include a dry anticoagulant, such as Heparin or EDTA, deposited on or within a portion of the collection module 14. In one embodiment, the material 40 is an open cell foam that contains dry anticoagulant dispersed within the cells of the open cell foam to promote the effectiveness of the flow-through mixing and anticoagulant uptake. In one embodiment, the sample stabilizer 24 is the dry anticoagulant powder 44.

In one embodiment, the open cell foam may be treated with an anticoagulant to form a dry anticoagulant powder finely distributed throughout the pores of the open cell foam.

As the blood sample 12 enters the collection module 14, the blood sample 12 passes through the open cell foam and is exposed to the anticoagulant powder available throughout the internal pore structure of the open cell foam. In this manner, the sample 12 dissolves and mixes with the dry anticoagulant powder 44 while passing through the material 40 or open cell foam.

The open cell foam may be a soft deformable open cell foam that is inert to blood, for example, a melamine foam, such as Basotect® foam commercially available from BASF, or may consist of a formaldehyde-melamine-sodium bisulfite copolymer. The open cell foam may also be a flexible, hydrophilic open cell foam that is substantially resistant to heat and organic solvents. In one embodiment, the foam may include a sponge material.

The anticoagulant or other additive may be introduced into the open cell foam by soaking the foam in a liquid solution of the additive and water and subsequently evaporating the water forming a dry additive powder finely distributed throughout the internal structure of the foam.

The collection module 14 includes a mixing chamber 22 that allows for passive mixing of the blood sample 12 with an anticoagulant or another additive, such as a blood stabilizer, as the blood sample 12 flows through the mixing chamber 22. In one embodiment, the mixing chamber 22 is disposed between the inlet port 32 and the outlet port 34.

The internal portion of the mixing chamber 22 may have any suitable structure or form as long as it provides for the mixing of the blood sample 12 with an anticoagulant or another additive as the blood sample 12 passes through the passageway 36 of the collection module 14. In one embodiment, the mixing chamber 22 includes a first curved wall 50 having a first inlet end 52 and a first exit end 54, and a second curved wall 56 having a second inlet end 58 and a second exit end 60. The first inlet end 52 is spaced a first distance D1 (FIG. 5) from the second inlet end 58 and the first exit end 54 is spaced a second distance D2 (FIG. 5) from the second exit end 60. In one embodiment, the second distance D2 is less than the first distance D1.

The mixing chamber 22 receives the sample 12 and the sample stabilizer 24 therein and effectuates distributed mixing of the sample stabilizer 24 within the sample 12. The mixing chamber 22 effectuates distributed mixing of the sample stabilizer 24 within the sample 12 and prevents a very high sample stabilizer concentration in any portion of the blood sample 12. This prevents underdosing of the sample stabilizer 24 in any portion of the blood sample 12. The mixing chamber 22 effectuates distributed mixing of the sample stabilizer 24 within the sample 12 so that an approximately equal amount and/or concentration of the sample stabilizer 24 is dissolved throughout the blood sample 12, e.g., an approximately equal amount and/or concentration of the sample stabilizer 24 is dissolved into the blood sample 12 from a front portion of the blood sample 12 to a rear portion of the blood sample 12.

In one embodiment, the collection module 14 includes a collection chamber 26 that is disposed between the mixing chamber 22 and the outlet port 34. In one embodiment, the collection chamber 26 includes a first deformable portion 62, a second deformable portion 64, and a rigid wall portion 66 (FIG. 1A) that is between the first deformable portion 62 and the second deformable portion 64. In one embodiment, the first deformable portion 62 is located on a first side 70 of the collection chamber 26 and the second deformable portion 64 is located on a second side 72 of the collection chamber 26. In one embodiment, the second side 72 of the collection chamber 26 is opposite from the first side 70 of the collection chamber 26.

Figure 5:
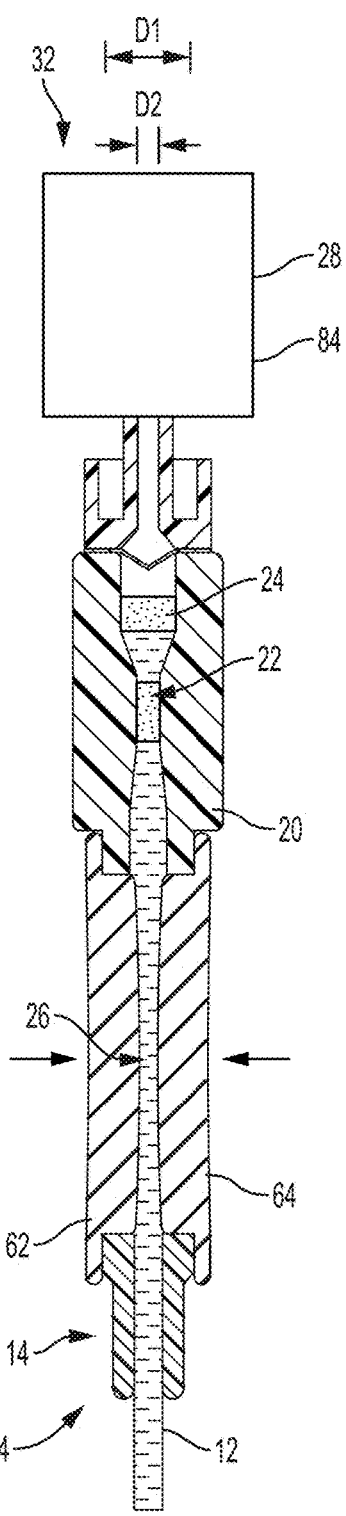
FIG. 5 is a cross-sectional side elevation view of a collection module with a deformable portion in a deformed position in accordance with an embodiment of the present invention.

The first deformable portion 62 and the second deformable portion 64 are transitionable between an initial position (FIGS. 1A-4) in which the sample 12 is contained within the collection chamber 26 and a deformed position (FIG. 5) in which a portion of the sample 12 is expelled from the collection chamber 26. The first deformable portion 62 and the second deformable portion 64 are simultaneously squeezed to transition from the initial position (FIGS. 1A-4) to the deformed position (FIG. 5).

Advantageously, by having a first deformable portion 62 and a second deformable portion 64 that can be simultaneously squeezed, a collection module 14 of the present disclosure is able to dispense more sample 12 out of the collection chamber 26 and the outlet port 34. Furthermore, in one embodiment, by having a first deformable portion 62 on a first side 70 and a second deformable portion 64 on an opposite second side 72, a collection module 14 of the present disclosure has a symmetrical design and provides a smooth straight fluid path chamber that encourages fluid attachment flow characteristics. The smooth straight fluid path chamber of the collection module 14 is without significant geometric steps in diameter and the smooth fluid pathway inhibits the formation of air pockets or bubbles.

After passing through the mixing chamber 22, the stabilized sample is directed to the collection chamber 26. The collection chamber 26 may take any suitable shape and size to store a sufficient volume of blood necessary for the desired testing, for example 500 µl or less. In one embodiment, the collection chamber 26 is defined by a portion of the housing 20 in combination with a first deformable portion 62, a second deformable portion 64, and a rigid wall portion 66.

The first deformable portion 62 and the second deformable portion 64 may be made of any material that is flexible, deformable, and capable of providing a fluid tight seal with the housing 20. In some embodiments, the first deformable portion 62 and the second deformable portion 64 may be made of natural or synthetic rubber, and other suitable elastomeric materials. The first deformable portion 62 and the second deformable portion 64 are secured to a portion of the housing 20 such that the first deformable portion 62 and the second deformable portion 64 are transitionable between an initial position (FIGS. 1A-4) in which the sample 12 is contained within the collection chamber 26 and a deformed position (FIG. 5) in which a portion of the sample 12 is expelled from the collection chamber 26.

In one embodiment, the collection module 14 includes a cap 30 that is removably attachable to the outlet port 34 and that protectively covers the outlet port 34. In one embodiment, the cap 30 includes a venting plug 80 which allows air to pass therethrough and prevents the sample 12 from passing therethrough.

The construction of the cap 30 and venting plug 80 allows air to pass through the cap 30 while preventing the blood sample 12 from passing through the cap 30 and may include a hydrophobic filter. The venting plug 80 has selected air passing resistance that may be used to finely control the filling rate of the passageway 36 and/or the collection chamber 26 of the collection module 14. By varying the porosity of the plug, the velocity of the air flow out of the cap 30, and thus the velocity of the blood sample flow into the collection module 14, may be controlled.

In one embodiment, the collection module 14 includes a closure 28 that is engaged with the inlet port 32 of the collection module 14 to seal the passageway 36. The closure 28 protectively covers the inlet port 32. The closure 28 allows for introduction of a blood sample 12 into the passageway 36 of the housing 20 and may include a pierceable self-sealing stopper 82 (FIG. 17) with an outer shield 84 such as a Hemogard™ cap commercially available from Becton, Dickinson and Company. The closure 28 also secures to the outer housing 16 which may be a vacuum containing blood collection tube such as a Vacutainer® blood collection tube commercially available from Becton, Dickinson and Company.

Figure 16:
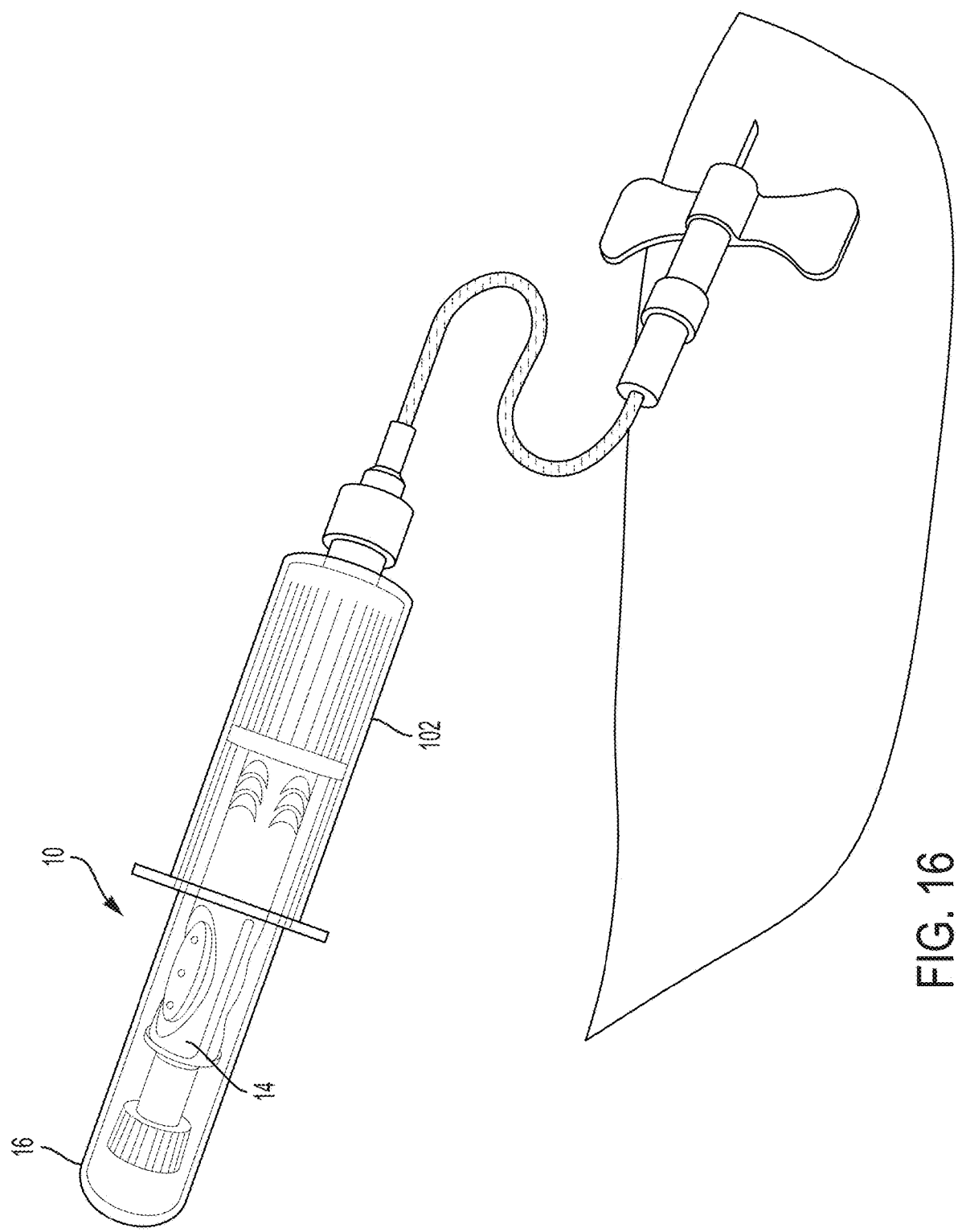
FIG. 16 is a perspective view of a biological fluid collection device inserted into a tube holder in accordance with an embodiment of the present invention.
Figure 17:
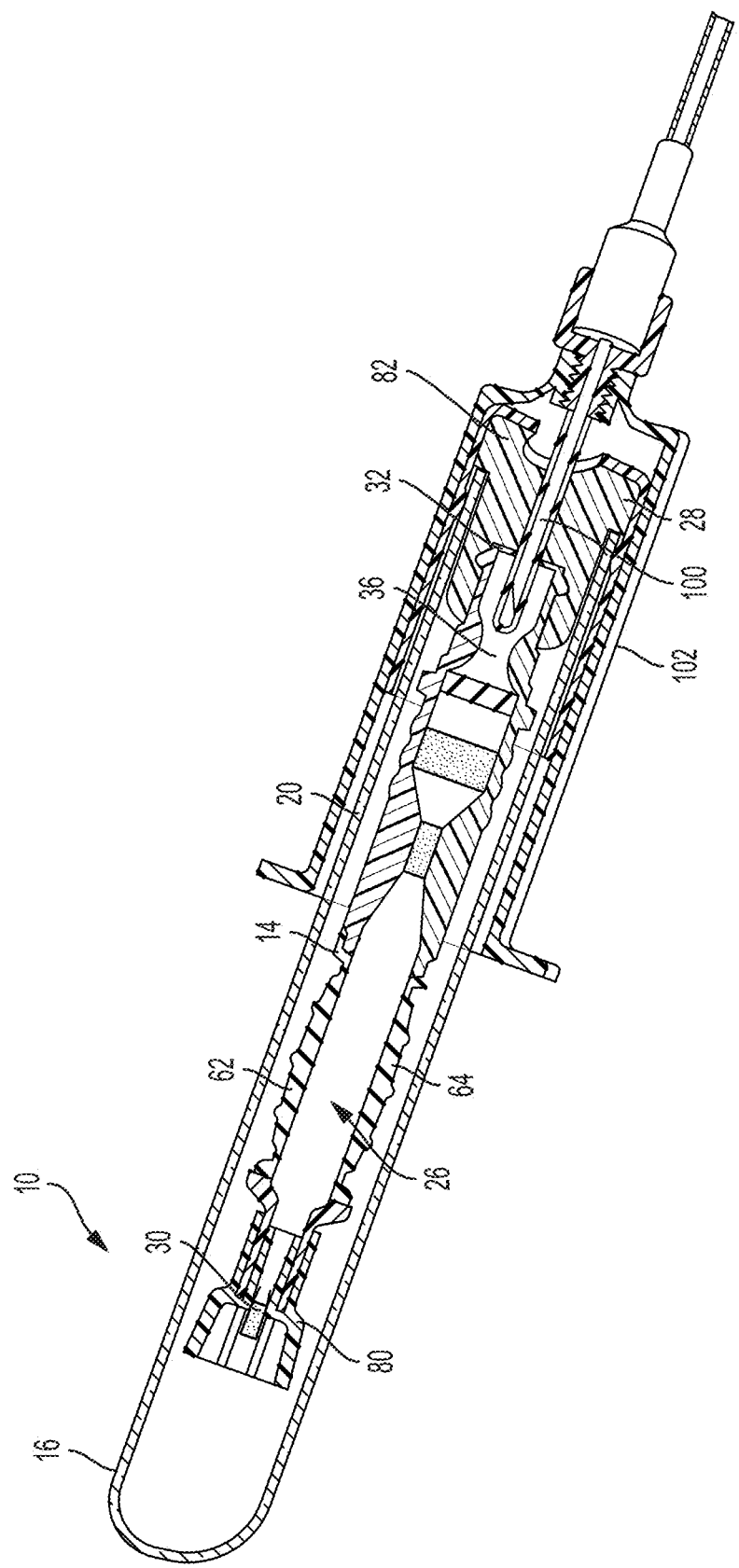
FIG. 17 is a cross-sectional perspective view of a biological fluid collection device inserted into a tube holder in accordance with an embodiment of the present invention.
Figure 18:
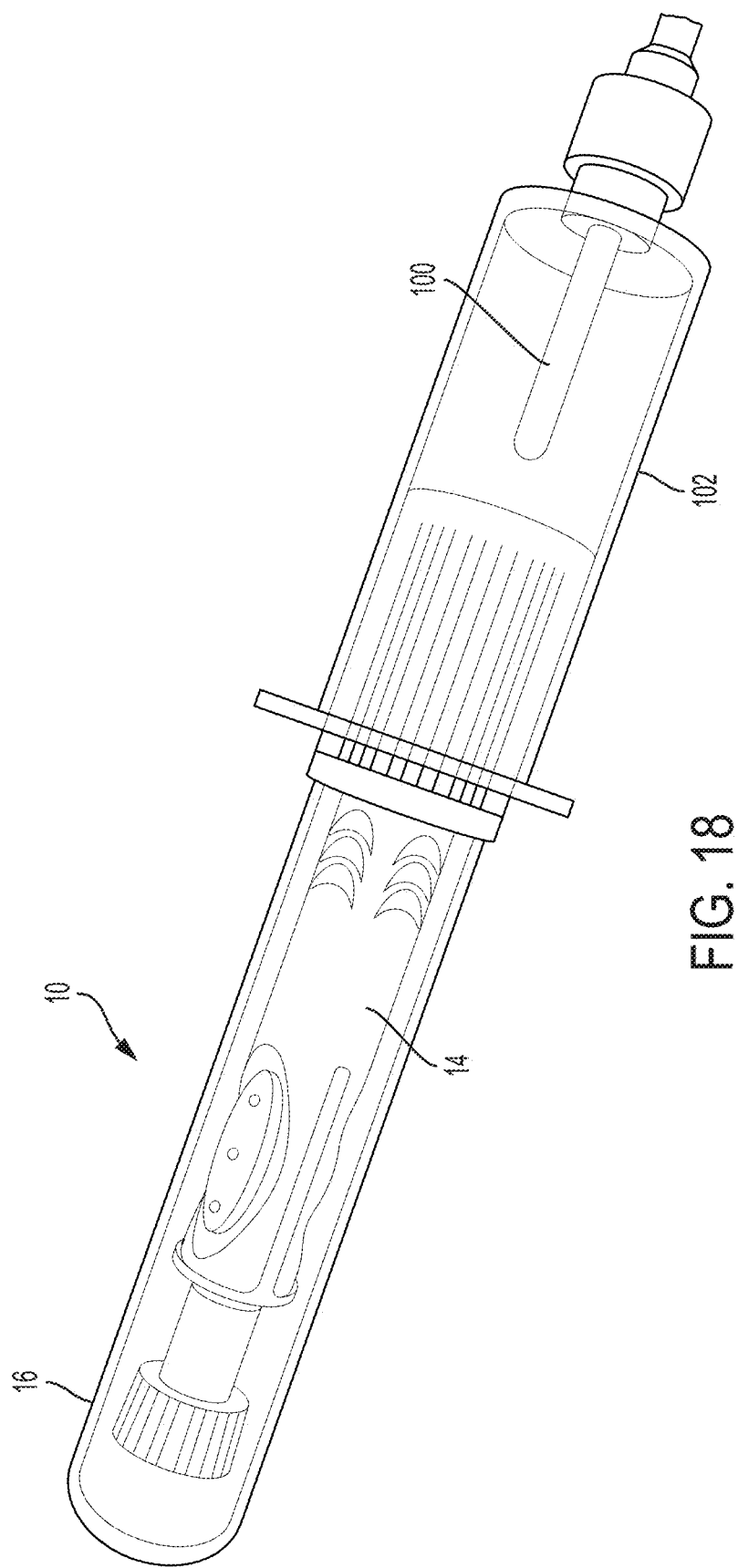
FIG. 18 is a perspective view of a biological fluid collection device being removed from a tube holder in accordance with an embodiment of the present invention.
Figure 19:
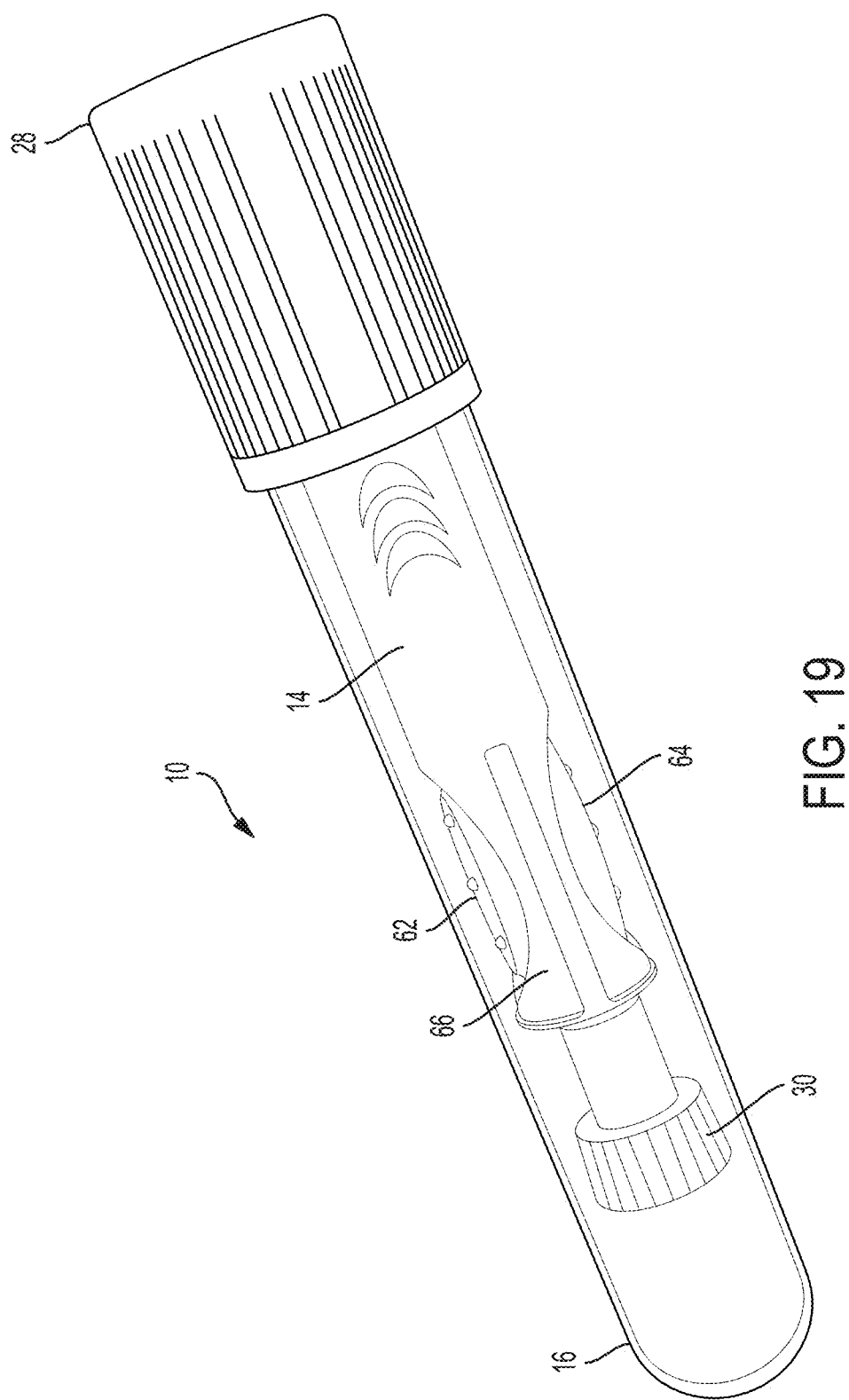
FIG. 19 is a perspective view of a biological fluid collection device in accordance with an embodiment of the present invention.

Referring to FIGS. 16-24, use of a biological fluid collection device 10 of the present disclosure will now be described. In use, a needle cannula 100 (FIGS. 17 and 18) is inserted into the passageway 36 of the housing 20 of the collection module 14 through the inlet port 32, such as through the pierceable self-sealing stopper 82 of closure 28. As shown in FIGS. 16-18, the biological fluid collection device 10 including the combined collection module 14 and the outer housing 16 may be inserted into a conventional tube holder 102 having a cannula 100 through which biological fluid, such as a blood sample 12, is passed.

The blood sample 12 is pulled into the passageway 36 of the housing 20 of the collection module 14 from the conventional tube holder 102 by the draw of the vacuum contained in the outer housing 16 (FIG. 17). In one embodiment, the blood sample 12 fills the entire passageway 36 such that, as the blood sample 12 enters the collection module 14, the blood sample 12 passes through the open cell foam, e.g., the material 40, and is exposed to the anticoagulant powder 44 available throughout the internal pore 42 structure of the open cell foam. In this manner, the sample 12 dissolves and mixes with the dry anticoagulant powder 44 while passing through the material 40 or open cell foam. Next, the mixing chamber 22 receives the sample 12 and the sample stabilizer 24 therein and effectuates distributed mixing of the sample stabilizer 24 within the sample 12. After passing through the mixing chamber 22, the stabilized sample is directed to the collection chamber 26. The collection chamber 26 may take any suitable shape and size to store a sufficient volume of blood necessary for the desired testing, for example 500 µl or less. In one embodiment, the cap 30 stops the collection of the blood sample 12 when the passageway 36, the mixing chamber 22, and the collection chamber 26 of the collection module 14 has been fully filled. The venting plug 80 of the cap 30 allows air to pass through the cap 30 while preventing the blood sample 12 from passing through the cap 30 into the outer housing 16.

In one embodiment, once sample collection is complete, the outer housing 16 including the collection module 14 is separated from the tube holder 102 (FIG. 18), and then the outer housing 16 is separated from the collection module 14 (FIG. 20) by removing the closure 28, which is still attached to the collection module 14, from the outer housing 16. Removal of the closure 28 may be accomplished by the user grasping both the outer shield 84 of the closure 28 and the outer housing 16 and pulling or twisting them in opposite directions.

Once the collection module 14 is separated from the outer housing 16, the cap 30 may then be removed from the collection module 14 (FIG. 21) exposing the outlet port 34 of the housing 20 of the collection module 14. Removal may be accomplished by the user grasping an exterior portion of the cap 30 and pulling the cap 30 from the housing 20. The blood sample 12 is held within the passageway 36 of the housing 20, e.g., the collection chamber 26, by capillary action after removal of the cap 30. In one embodiment, alternatively, removal of the cap 30 may occur upon removal of the collection module 14 from the outer housing 16. In this configuration, the cap 30 is restrained within the outer housing 16. In one embodiment, the cap 30 may be engaged with the outer housing 16 so that the outer housing 16 and the cap 30 are removed in a single step.

Figure 24:
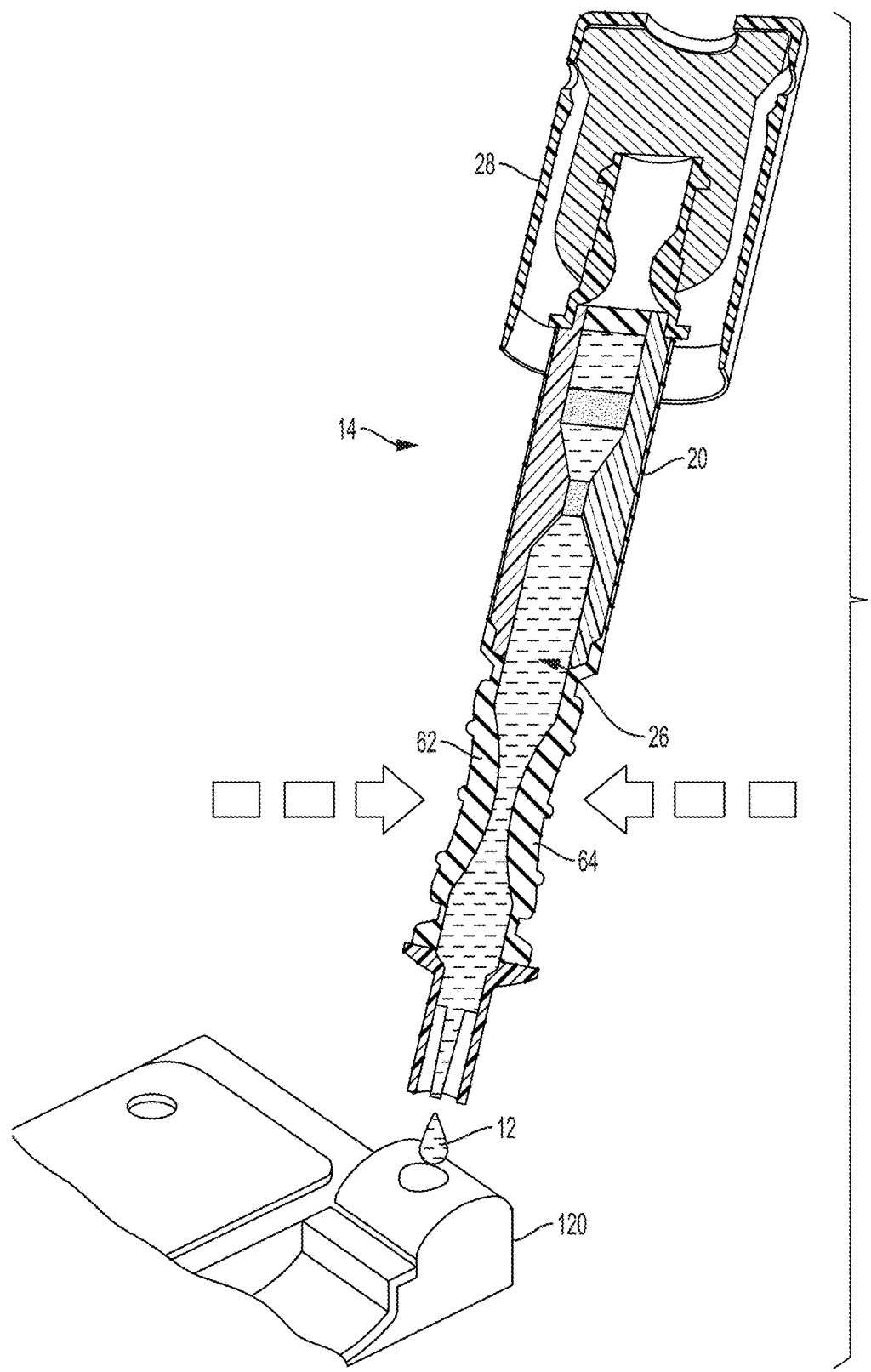
FIG. 24 is a cross-sectional perspective view of a collection module with a deformable portion in a deformed position adjacent a point-of-care testing device in accordance with an embodiment of the present invention.

The blood sample 12 may then be dispensed from the collection module 14 by activation of the first deformable portion 62 and the second deformable portion 64. For example, the first deformable portion 62 and the second deformable portion 64 are transitionable between an initial position (FIGS. 1A-4 and 21-23) in which the sample 12 is contained within the collection chamber 26 and a deformed position (FIGS. 5 and 24) in which a portion of the sample 12 is expelled from the collection chamber 26 and the outlet port 34. The first deformable portion 62 and the second deformable portion 64 are simultaneously squeezed to transition from the initial position (FIGS. 1A-4 and 21-23) to the deformed position (FIGS. 5 and 24). In this manner, the blood sample 12 may be transferred to a device intended to analyze the sample, e.g., such as a point-of-care testing device 120 (FIGS. 23 and 24), a cartridge tester, or a near patient testing device, while minimizing the exposure of the medical practitioner to the blood sample.

Advantageously, by having a first deformable portion 62 and a second deformable portion 64 that can be simultaneously squeezed, a collection module 14 of the present disclosure is able to dispense more sample 12 out of the collection chamber 26 and the outlet port 34. Furthermore, in one embodiment, by having a first deformable portion 62 on a first side 70 and a second deformable portion 64 on an opposite second side 72, a collection module 14 of the present disclosure has a symmetrical design and provides a smooth straight fluid path chamber that encourages fluid attachment flow characteristics.

Figure 6:
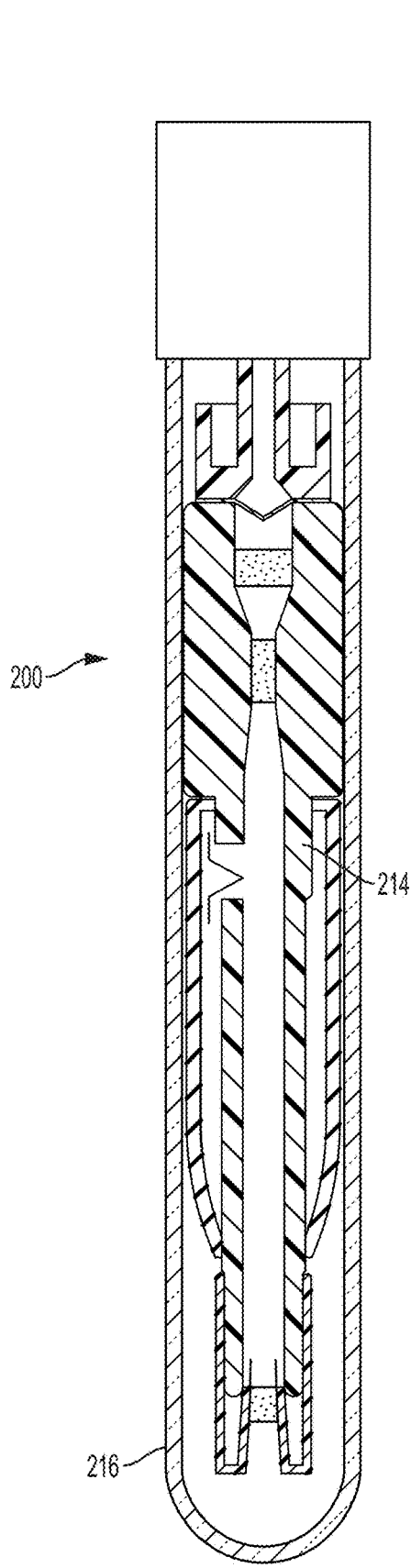
FIG. 6 is a cross-sectional side elevation view of a biological fluid collection device in accordance with another embodiment of the present invention.
Figure 7:
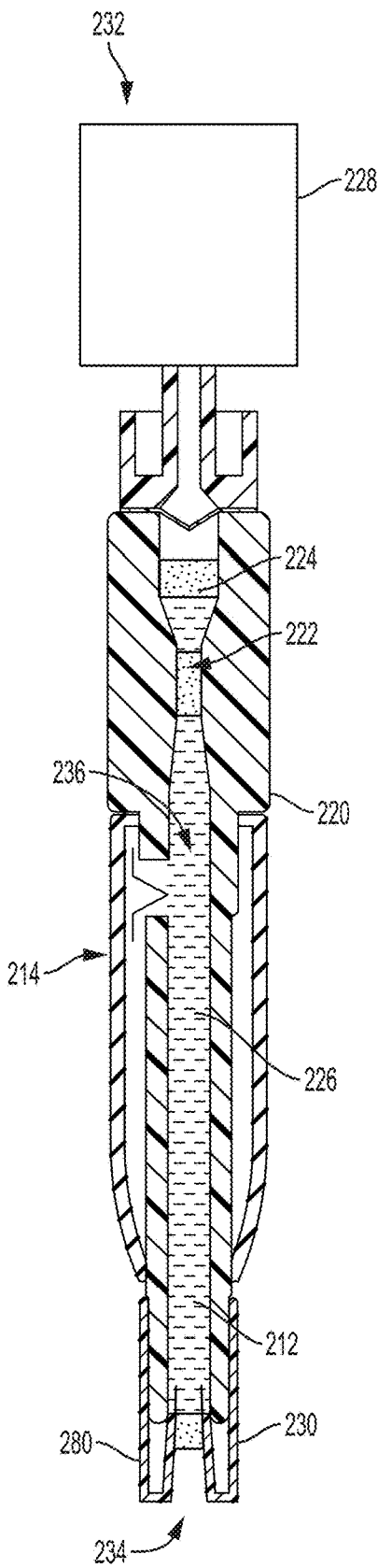
FIG. 7 is a cross-sectional side elevation view of a collection module with a cap in accordance with another embodiment of the present invention.
Figure 10:
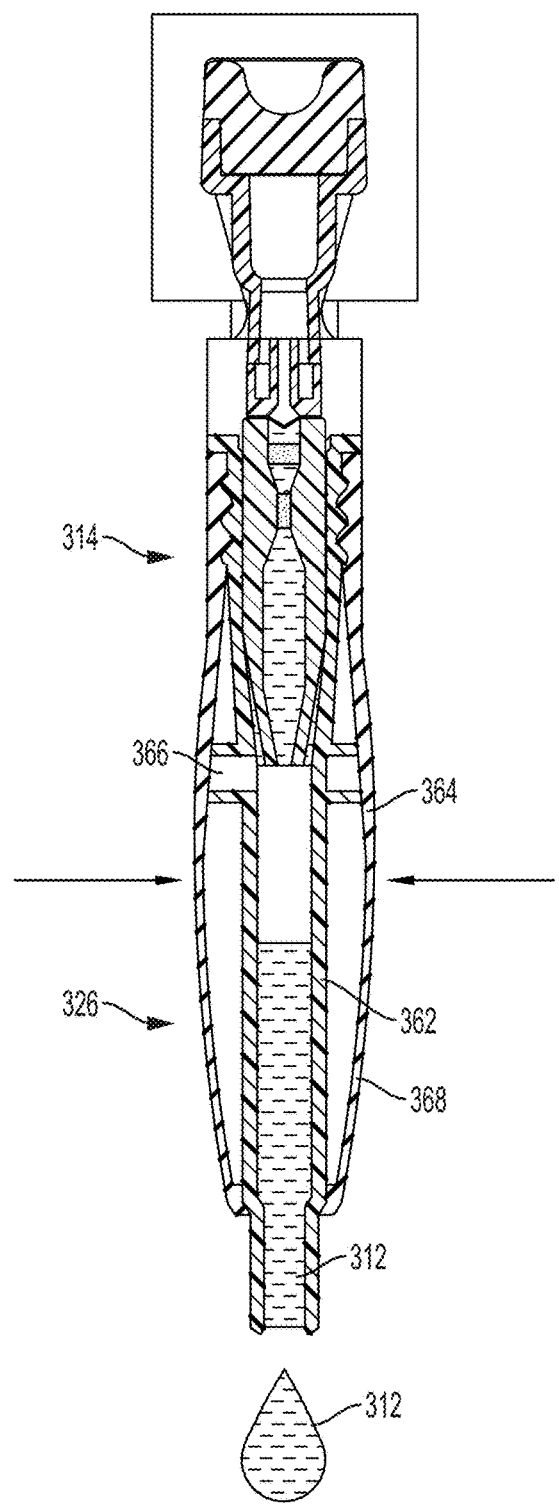
FIG. 10 is a cross-sectional side elevation view of a collection module in accordance with another embodiment of the present invention.

FIGS. 6-10 illustrate another exemplary embodiment of a biological fluid collection device of the present disclosure. Referring to FIG. 6, a biological fluid collection device 200 of the present disclosure is adapted to receive a biological fluid sample, such as a blood sample 212, and includes a collection module 214 and an outer housing 216 that is removably connectable to the collection module 214. In one embodiment, with the collection module 214 connected to the outer housing 216, the collection module 214 is disposed within the outer housing 216 as shown in FIG. 6.

Referring to FIGS. 6-10, in one embodiment, the collection module 214 of the present disclosure is adapted to receive a biological fluid sample, such as a blood sample 212, and includes a housing 220, a mixing chamber 222, a sample stabilizer 224, a collection chamber 226, a closure 228, and a cap 230.

In one embodiment, the housing 220 of the collection module 14 includes an inlet port 232 and an outlet port 234. In one embodiment, the inlet port 232 and the outlet port 234 are in fluid communication via a passageway 236 extending therebetween.

The mixing chamber 222 and the collection chamber 226 are provided in fluid communication via the passageway 236. The mixing chamber 222 and the collection chamber 226 are positioned such that a biological fluid sample, such as a blood sample 212, introduced into the inlet port 232 of the collection module 214 will first pass through a sample stabilizer 224, then the blood sample 212 and the sample stabilizer 224 pass through the mixing chamber 222, and subsequently the sample 212 with the sample stabilizer 224 properly mixed therein flow into the collection chamber 226, prior to reaching the outlet port 234 of the collection module 214. In this way, the blood sample 212 may be mixed with a sample stabilizer 224, such as an anticoagulant or other additive, provided within the collection module 214, before passing through the mixing chamber 222 for proper mixing of the sample stabilizer 224 within the blood sample 212, and then the stabilized sample is received and stored within the collection chamber 226.

In one embodiment, a sample stabilizer 224 is disposed between the inlet port 232 and the mixing chamber 222. The collection module 214 of the present disclosure provides passive and fast mixing of a blood sample 212 with the sample stabilizer 224. For example, the collection module 214 includes a mixing chamber 222 that allows for passive mixing of the blood sample 212 with an anticoagulant or another additive, such as a blood stabilizer, as the blood sample 212 flows through the mixing chamber 222.

The sample stabilizer can be an anticoagulant, or a substance designed to preserve a specific element within the blood such as, for example, RNA, protein analyte, or other element. In one embodiment, the sample stabilizer 224 is disposed between the inlet port 232 and the mixing chamber 222. In other embodiments, the sample stabilizer 224 may be disposed in other areas within the housing 220 of the collection module 214.

Referring to FIGS. 14 and 15, in one embodiment, the collection module 214 includes a material 240 including pores 242 that is disposed between the inlet port 232 and the mixing chamber 222 and a dry anticoagulant powder 244 that is within the pores 242 of the material 240. In this manner, the collection module 214 may include a dry anticoagulant, such as Heparin or EDTA, deposited on or within a portion of the collection module 214. In one embodiment, the material 240 is an open cell foam that contains dry anticoagulant dispersed within the cells of the open cell foam to promote the effectiveness of the flow-through mixing and anticoagulant uptake. In one embodiment, the sample stabilizer 224 is the dry anticoagulant powder 244.

In one embodiment, the open cell foam may be treated with an anticoagulant to form a dry anticoagulant powder finely distributed throughout the pores of the open cell foam. As the blood sample 212 enters the collection module 214, the blood sample 212 passes through the open cell foam and is exposed to the anticoagulant powder available throughout the internal pore structure of the open cell foam. In this manner, the sample 212 dissolves and mixes with the dry anticoagulant powder 244 while passing through the material 240 or open cell foam.

The open cell foam may be a soft deformable open cell foam that is inert to blood, for example, a melamine foam, such as Basotect® foam commercially available from BASF, or may consist of a formaldehyde-melamine-sodium bisulfite copolymer. The open cell foam may also be a flexible, hydrophilic open cell foam that is substantially resistant to heat and organic solvents. In one embodiment, the foam may include a sponge material.

The anticoagulant or other additive may be introduced into the open cell foam by soaking the foam in a liquid solution of the additive and water and subsequently evaporating the water forming a dry additive powder finely distributed throughout the internal structure of the foam.

The collection module 214 includes a mixing chamber 222 that allows for passive mixing of the blood sample 212 with an anticoagulant or another additive, such as a blood stabilizer, as the blood sample 212 flows through the mixing chamber 222. In one embodiment, the mixing chamber 222 is disposed between the inlet port 232 and the outlet port 234.

The internal portion of the mixing chamber 222 may have any suitable structure or form as long as it provides for the mixing of the blood sample 212 with an anticoagulant or another additive as the blood sample 212 passes through the passageway 236 of the collection module 214. In one embodiment, the mixing chamber 222 includes a first curved wall 250 having a first inlet end 252 and a first exit end 254, and a second curved wall 256 having a second inlet end 258 and a second exit end 260. The first inlet end 252 is spaced a first distance D1 (FIG. 9) from the second inlet end 258 and the first exit end 254 is spaced a second distance D2 (FIG. 9) from the second exit end 260. In one embodiment, the second distance D2 is less than the first distance D1.

The mixing chamber 222 receives the sample 212 and the sample stabilizer 224 therein and effectuates distributed mixing of the sample stabilizer 224 within the sample 212. The mixing chamber 222 effectuates distributed mixing of the sample stabilizer 224 within the sample 212 and prevents a very high sample stabilizer concentration in any portion of the blood sample 212. This prevents underdosing of the sample stabilizer 224 in any portion of the blood sample 212. The mixing chamber 222 effectuates distributed mixing of the sample stabilizer 224 within the sample 212 so that an approximately equal amount and/or concentration of the sample stabilizer 224 is dissolved throughout the blood sample 212, e.g., an approximately equal amount and/or concentration of the sample stabilizer 224 is dissolved into the blood sample 212 from a front portion of the blood sample 212 to a rear portion of the blood sample 212.

In one embodiment, the collection module 214 includes a collection chamber 226 that is disposed between the mixing chamber 222 and the outlet port 234. In one embodiment, the collection chamber 226 includes a rigid wall chamber 262 that receives the sample 212, a deformable portion 264 including air, and a one-way valve 266 disposed between the rigid wall chamber 262 and the deformable portion 264. In one embodiment, the deformable portion 264 is external to the rigid wall chamber 262. In one embodiment, the deformable portion 264 is an air bladder 268. In this manner, the collection module 214 uses a bladder filled with air or viscous fluid to displace a sample out of the collection module 214.

The deformable portion 264 is transitionable between an initial position (FIGS. 6-8) in which the sample 212 is contained within the rigid wall chamber 262 and a deformed position (FIG. 9) in which a portion of the sample 212 is expelled from the rigid wall chamber 262. The deformable portion 264 is squeezed to transition from the initial position (FIGS. 6-8) to the deformed position (FIG. 9).

In one embodiment, the one-way valve 266 prevents the sample 212 from moving from the rigid wall chamber 262 to the deformable portion 264 and allows air to move from the deformable portion 264 to the rigid wall chamber 262 to expel the sample 212 from the rigid wall chamber 262.

In one embodiment, the one-way valve 266 is used to keep a distal meniscus static (non-receding) when the bladder 268 is not being squeezed. Without the one-way valve 266, negative pressure in the bladder 268 would suck back the sample's blood meniscus after the user released his squeeze on the bladder 268. The collection module 214 of the present disclosure provides for controlled dispensing of the meniscus.

In one embodiment, the collection module 214 is designed to leverage an effectively constant diameter for the dispensing portion of the fluid pathway. This effectively constant diameter avoids the formation of air bubbles within the collection module 214.

After passing through the mixing chamber 222, the stabilized sample is directed to the collection chamber 226. The collection chamber 226 may take any suitable shape and size to store a sufficient volume of blood necessary for the desired testing, for example 500 µl or less.

In one embodiment, the collection module 214 includes a cap 230 that is removably attachable to the outlet port 234 and that protectively covers the outlet port 234. In one embodiment, the cap 230 includes a venting plug 280 which allows air to pass therethrough and prevents the sample 212 from passing therethrough.

The construction of the cap 230 and venting plug 280 allows air to pass through the cap 230 while preventing the blood sample 212 from passing through the cap 230 and may include a hydrophobic filter. The venting plug 280 has selected air passing resistance that may be used to finely control the filling rate of the passageway 236 and/or the collection chamber 226 of the collection module 214. By varying the porosity of the plug, the velocity of the air flow out of the cap 230, and thus the velocity of the blood sample flow into the collection module 214, may be controlled.

In one embodiment, the collection module 214 includes a closure 228 that is engaged with the inlet port 232 of the collection module 214 to seal the passageway 236. The closure 228 protectively covers the inlet port 232. The closure 228 allows for introduction of a blood sample 212 into the passageway 236 of the housing 220 and may include a pierceable self-sealing stopper with an outer shield such as a Hemogard™ cap commercially available from Becton, Dickinson and Company. The closure 228 also secures to the outer housing 216 which may be a vacuum containing blood collection tube such as a Vacutainer® blood collection tube commercially available from Becton, Dickinson and Company.

Use of a biological fluid collection device 200 of the present disclosure is similar to the use of a biological fluid collection device 10 as described above with reference to FIGS. 16-24. In use, a needle cannula 100 (FIGS. 17 and 18) is inserted into the passageway 236 of the housing 220 of the collection module 214 through the inlet port 232, such as through the pierceable self-sealing stopper of closure 228. The biological fluid collection device 200 including the combined collection module 214 and the outer housing 216 may be inserted into a conventional tube holder 102 (FIGS. 16-18) having a cannula 100 through which biological fluid, such as a blood sample 212, is passed.

The blood sample 212 is pulled into the passageway 236 of the housing 220 of the collection module 214 from the conventional tube holder 102 by the draw of the vacuum contained in the outer housing 216. In one embodiment, the blood sample 212 fills the entire passageway 236 such that, as the blood sample 212 enters the collection module 214, the blood sample 212 passes through the open cell foam and is exposed to the anticoagulant powder available throughout the internal pore structure of the open cell foam. In this manner, the sample 212 dissolves and mixes with the dry anticoagulant powder 244 while passing through the material 240 or open cell foam. Next, the mixing chamber 222 receives the sample 212 and the sample stabilizer 224 therein and effectuates distributed mixing of the sample stabilizer 224 within the sample 212. After passing through the mixing chamber 222, the stabilized sample is directed to the collection chamber 226. The collection chamber 226 may take any suitable shape and size to store a sufficient volume of blood necessary for the desired testing, for example 500 µl or less. In one embodiment, the cap 230 stops the collection of the blood sample 212 when the passageway 236, the mixing chamber 222, and the collection chamber 226 of the collection module 214 has been fully filled. The venting plug 280 of the cap 230 allows air to pass through the cap 230 while preventing the blood sample 212 from passing through the cap 230 into the outer housing 216.

Figure 20:
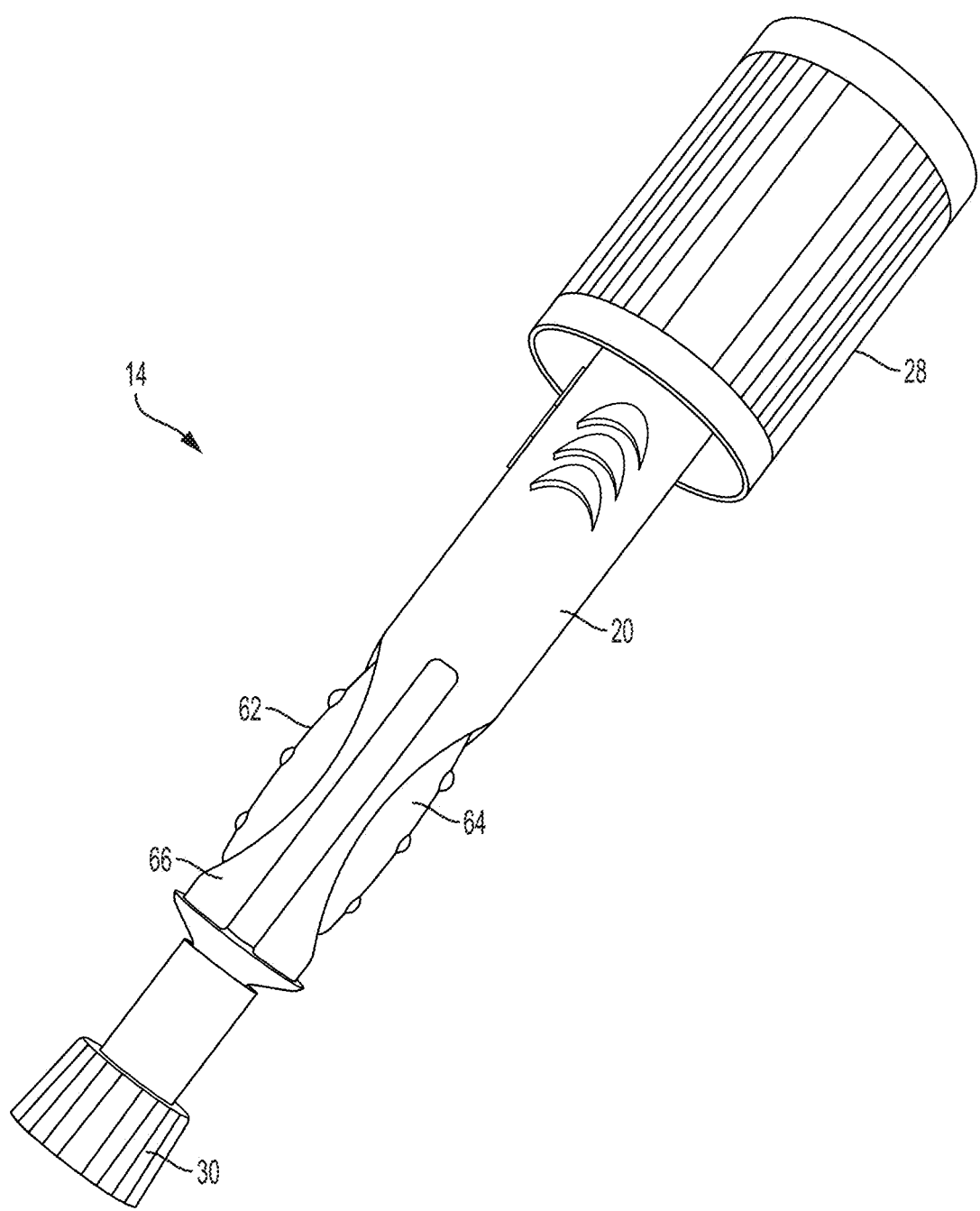
FIG. 20 is a perspective view of a collection module in accordance with an embodiment of the present invention.

In one embodiment, once sample collection is complete, the outer housing 216 including the collection module 214 is separated from the tube holder 102 (similarly as shown in FIG. 18), and then the outer housing 216 is separated from the collection module 214 (similarly as shown in FIG. 20) by removing the closure 228, which is still attached to the collection module 214, from the outer housing 216. Removal of the closure 228 may be accomplished by the user grasping both the outer shield of the closure 228 and the outer housing 216 and pulling or twisting them in opposite directions.

Figure 21:
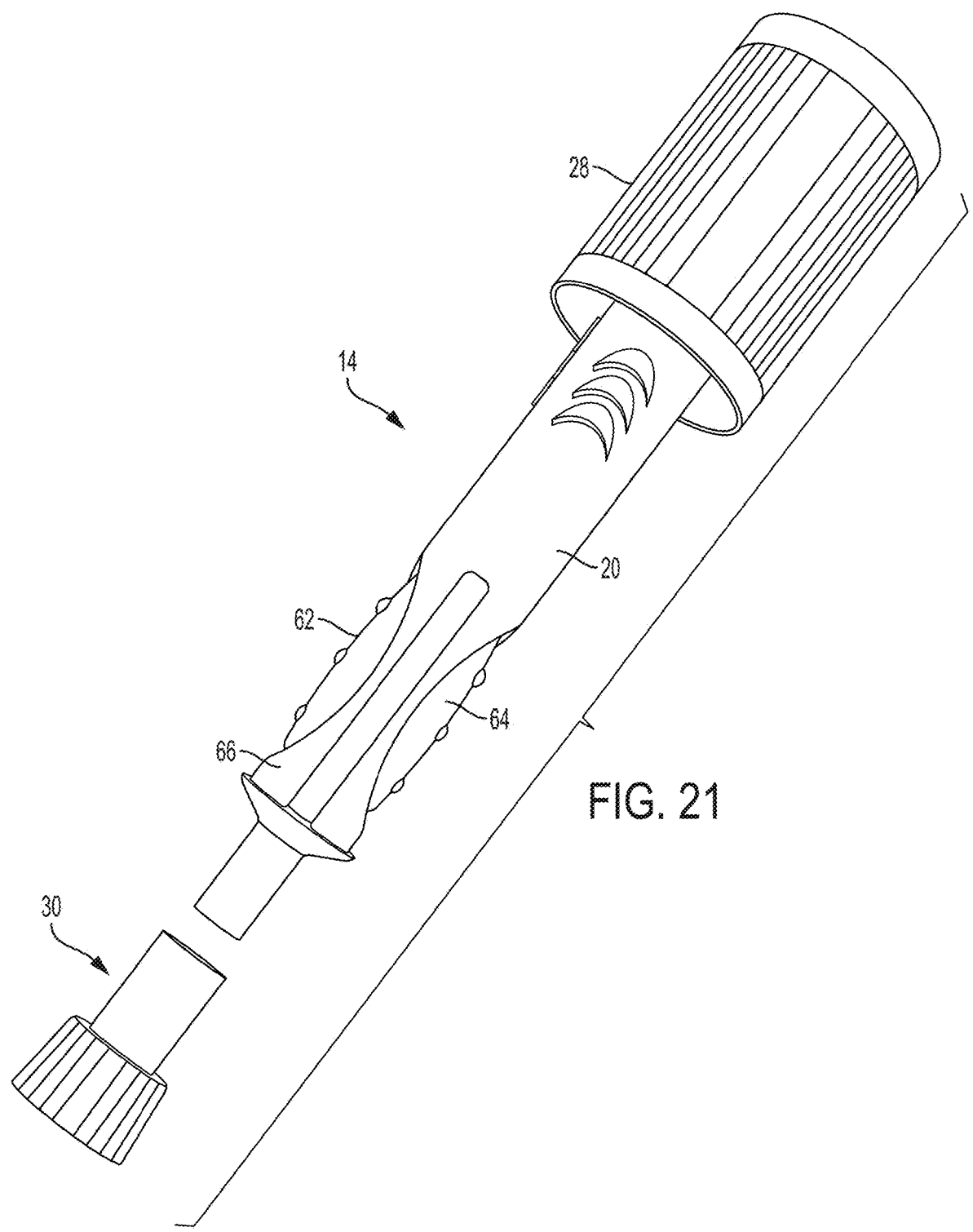
FIG. 21 is a perspective view of a cap being removed from a collection module in accordance with an embodiment of the present invention.
Figure 22:
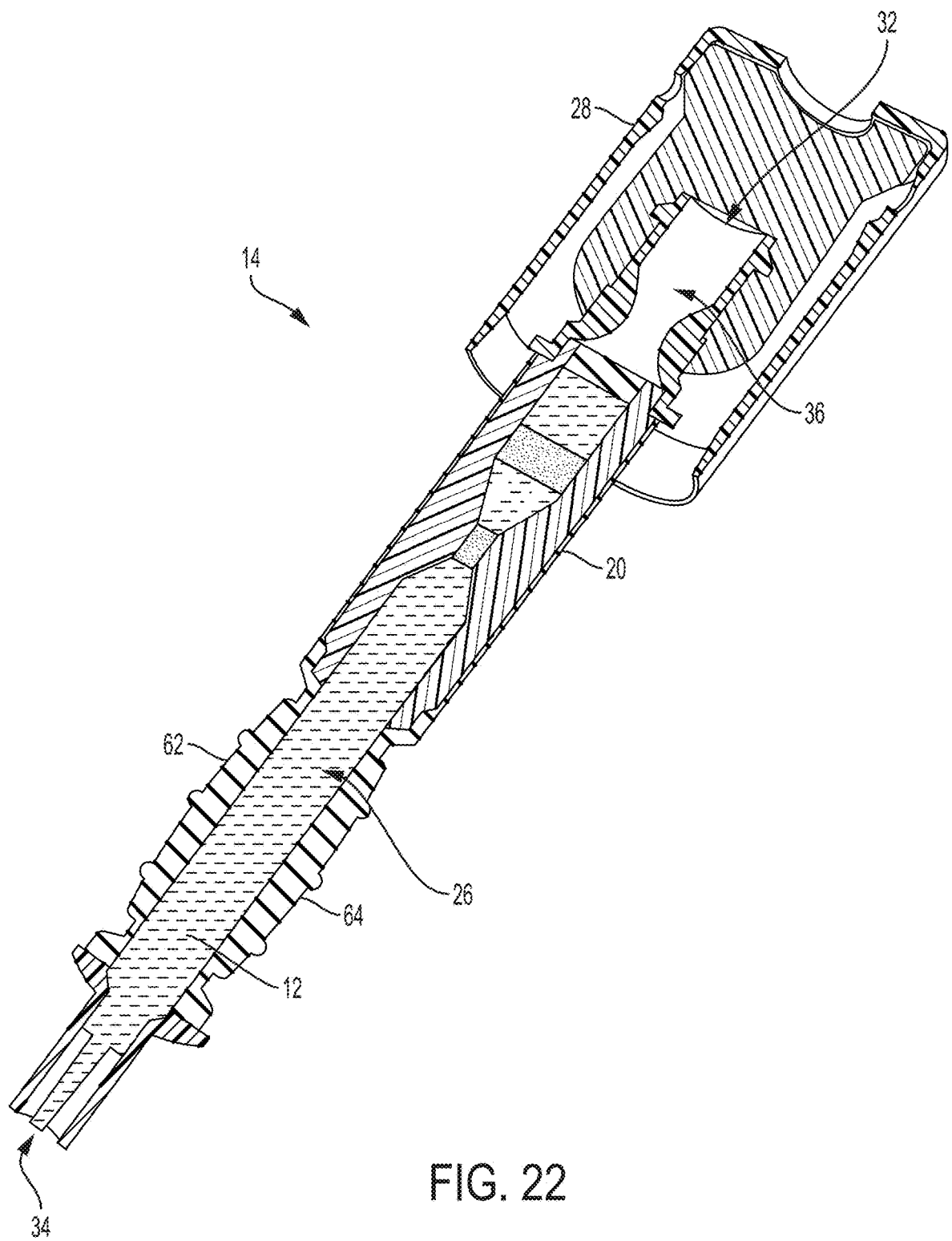
FIG. 22 is a cross-sectional perspective view of a collection module in accordance with an embodiment of the present invention.
Figure 23:
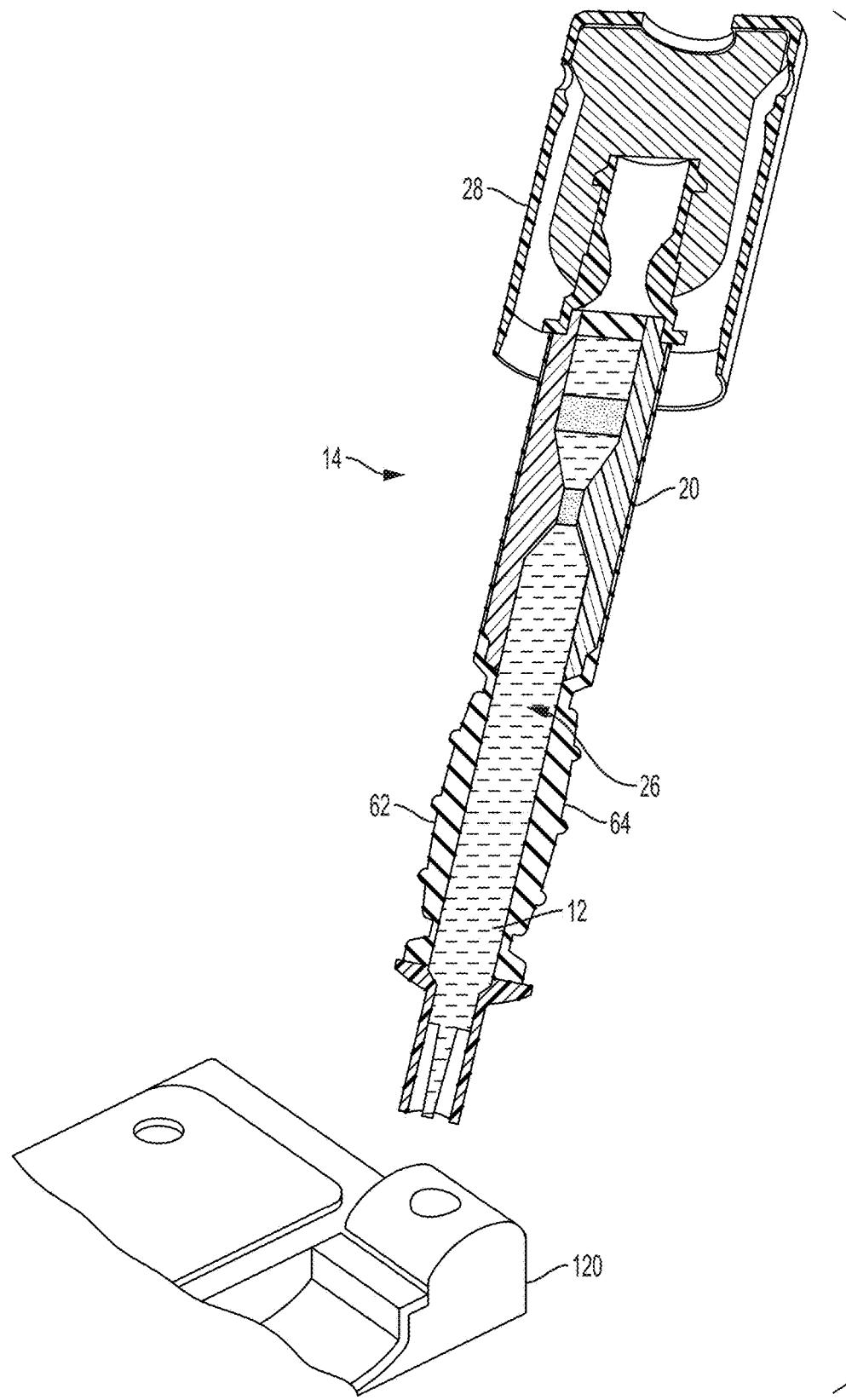
FIG. 23 is a cross-sectional perspective view of a collection module with a deformable portion in an initial position adjacent a point-of-care testing device in accordance with an embodiment of the present invention.

Once the collection module 214 is separated from the outer housing 216, the cap 230 may then be removed from the collection module 214 (similarly as shown in FIG. 21) exposing the outlet port 234 of the housing 220 of the collection module 214. Removal may be accomplished by the user grasping an exterior portion of the cap 230 and pulling the cap 230 from the housing 220. The blood sample 212 is held within the passageway 236 of the housing 220, e.g., the collection chamber 226, by capillary action after removal of the cap 230. In one embodiment, alternatively, removal of the cap 230 may occur upon removal of the collection module 214 from the outer housing 216. In this configuration, the cap 230 is restrained within the outer housing 216. In one embodiment, the cap 230 may be engaged with the outer housing 216 so that the outer housing 216 and the cap 230 are removed in a single step.

The blood sample 212 may then be dispensed from the collection module 214 by activation of the deformable portion 264. For example, the deformable portion 264 is transitionable between an initial position (FIGS. 6-8) in which the sample 212 is contained within the rigid wall chamber 262 and a deformed position (FIG. 9) in which a portion of the sample 212 is expelled from the rigid wall chamber 262. The deformable portion 264 is squeezed to transition from the initial position (FIGS. 6-8) to the deformed position (FIG. 9). In this manner, the blood sample 212 may be transferred to a device intended to analyze the sample, e.g., such as a point-of-care testing device 120 (FIG. 24), a cartridge tester, or a near patient testing device, while minimizing the exposure of the medical practitioner to the blood sample.

In one embodiment, the one-way valve 266 prevents the sample 212 from moving from the rigid wall chamber 262 to the deformable portion 264 and allows air to move from the deformable portion 264 to the rigid wall chamber 262 to expel the sample 212 from the rigid wall chamber 262.

Figure 11:
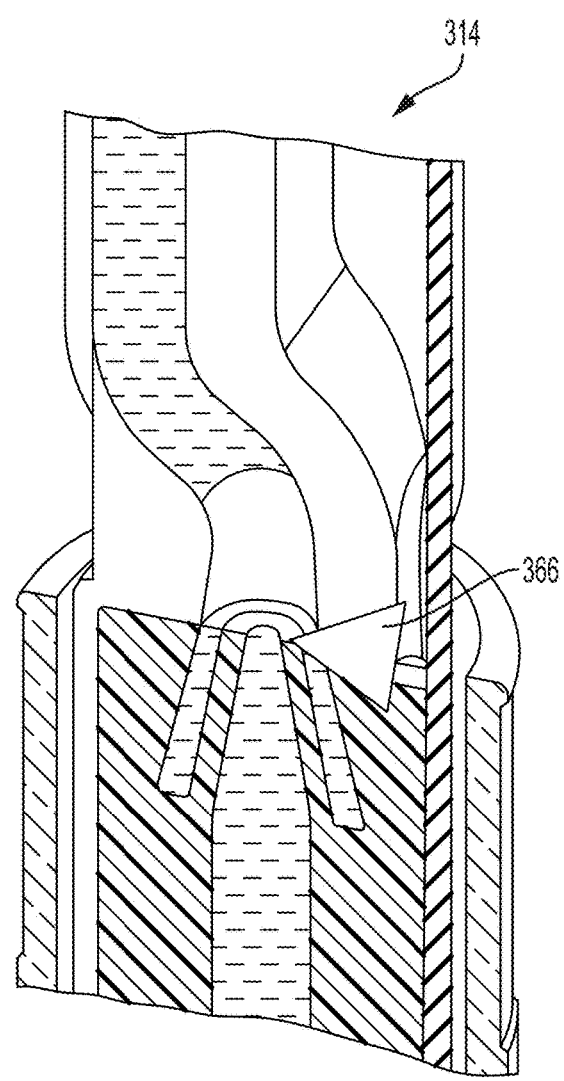
FIG. 11 is a partial cross-sectional view of a portion of a collection chamber in accordance with another embodiment of the present invention.

FIGS. 11-13 illustrate another exemplary embodiment of a biological fluid collection device of the present disclosure. The embodiment illustrated in FIGS. 11-13 includes similar components to the embodiment illustrated in FIGS. 6-10. For the sake of brevity, these similar components and the similar steps of using collection module 314 (FIGS. 11-13) will not all be discussed in conjunction with the embodiment illustrated in FIGS. 11-13.

Referring to FIGS. 11-13, in one embodiment, the collection module 314 includes a collection chamber 326. In one embodiment, the collection chamber 326 includes a rigid wall chamber 362 that receives the sample 312, a deformable portion 364 including air, and a one-way valve 366 disposed between the rigid wall chamber 362 and the deformable portion 364. In one embodiment, the deformable portion 364 is external to the rigid wall chamber 362. In one embodiment, the deformable portion 364 is an air bladder 368. In this manner, the collection module 314 uses a bladder filled with air or viscous fluid to displace a sample out of the collection module 314.

The deformable portion 364 is transitionable between an initial position (FIG. 12) in which the sample 312 is contained within the rigid wall chamber 362 and a deformed position (FIG. 13) in which a portion of the sample 312 is expelled from the rigid wall chamber 362. The deformable portion 364 is squeezed to transition from the initial position (FIG. 12) to the deformed position (FIG. 13).

In one embodiment, the one-way valve 366 prevents the sample 312 from moving from the rigid wall chamber 362 to the deformable portion 364 and allows air to move from the deformable portion 364 to the rigid wall chamber 362 to expel the sample 312 from the rigid wall chamber 362.

In one embodiment, the one-way valve 366 is used to keep a distal meniscus static (non-receding) when the bladder 368 is not being squeezed. Without the one-way valve 366, negative pressure in the bladder 368 would suck back the sample's blood meniscus after the user released his squeeze on the bladder 368. The collection module 314 of the present disclosure provides for controlled dispensing of the meniscus.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A collection module adapted to receive a sample, the collection module comprising:
   a housing having an inlet port and an outlet port, the inlet port and the outlet port in fluid communication;
   a mixing chamber disposed between the inlet port and the outlet port;
   a sample stabilizer disposed between the inlet port and the outlet port; and
   a collection chamber disposed between the mixing chamber and the outlet port, the collection chamber including a first deformable portion and a second deformable portion, wherein the mixing chamber receives the sample and at least a portion of the sample stabilizer therein,
   wherein the collection chamber further comprises a rigid wall portion between the first deformable portion and the second deformable portion.

2. The collection module of claim 1, wherein the first deformable portion and the second deformable portion are transitionable between an initial position in which the sample is contained within the collection chamber and a deformed position in which a portion of the sample is expelled from the collection chamber.

3. The collection module of claim 2, wherein the first deformable portion and the second deformable portion are simultaneously squeezed to transition from the initial position to the deformed position.

4. The collection module of claim 1, wherein the mixing chamber further comprises:
   a first curved wall having a first inlet end and a first exit end; and
   a second curved wall having a second inlet end and a second exit end,
   wherein the first inlet end is spaced a first distance from the second inlet end, and
   wherein the first exit end is spaced a second distance from the second exit end, the second distance less than the first distance.

5. The collection module of claim 1, further comprising:
   a material including pores disposed between the inlet port and the mixing chamber; and
   a dry anticoagulant powder within the pores of the material.

6. The collection module of claim 5, wherein the sample dissolves and mixes with the dry anticoagulant powder while passing through the material.

7. The collection module of claim 5, wherein the material is an open cell foam.

8. The collection module of claim 5, wherein the sample stabilizer is the dry anticoagulant powder.

9. The collection module of claim 1, further comprising a closure covering the inlet port.

10. The collection module of claim 1, further comprising a cap covering the outlet port and having a venting plug which allows air to pass therethrough and prevents the sample from passing therethrough.

11. A biological fluid collection device, comprising:
    the collection module of claim 1; and
    an outer housing removably connectable to the collection module,
    wherein, with the collection module connected to the outer housing, the collection module is disposed within the outer housing.

12. A collection module adapted to receive a sample, the collection module comprising:
    a housing having an inlet port and an outlet port, the inlet port and the outlet port in fluid communication;
    a mixing chamber disposed between the inlet port and the outlet port;
    a sample stabilizer disposed between the inlet port and the mixing chamber; and
    a collection chamber disposed between the mixing chamber and the outlet port, the collection chamber comprising:
       a rigid wall chamber that receives the sample;
       a deformable portion including air, the deformable portion external to the rigid wall chamber; and
       a one-way valve between the rigid wall chamber and the deformable portion,
       wherein the deformable portion is transitionable between an initial position in which the sample is contained within the rigid wall chamber and a deformed position in which a portion of the sample is expelled from the rigid wall chamber, and
       wherein the one-way valve prevents the sample from moving from the rigid wall chamber to the deformable portion and allows air to move from the deformable portion to the rigid wall chamber to expel the sample from the rigid wall chamber.

13. The collection module of claim 12, wherein the deformable portion comprises a bladder.

14. The collection module of claim 12, wherein the mixing chamber receives the sample and the sample stabilizer therein.

15. The collection module of claim 12, wherein the mixing chamber further comprises:

a first curved wall having a first inlet end and a first exit end; and a second curved wall having a second inlet end and a second exit end, wherein the first inlet end is spaced a first distance from the second inlet end, and wherein the first exit end is spaced a second distance from the second exit end, the second distance less than the first distance.

16. The collection module of claim 12, further comprising:

a material including pores disposed between the inlet port and the mixing chamber; and a dry anticoagulant powder within the pores of the material.

17. The collection module of claim 16, wherein the sample dissolves and mixes with the dry anticoagulant powder while passing through the material.

18. The collection module of claim 16, wherein the material is an open cell foam.

19. The collection module of claim 16, wherein the sample stabilizer is the dry anticoagulant powder.

\* \* \* \* \*